(12) United States Patent
Nishide et al.

(10) Patent No.: US 8,009,890 B2
(45) Date of Patent: Aug. 30, 2011

(54) IMAGE DISPLAY APPARATUS AND X-RAY CT APPARATUS

(75) Inventors: Akihiko Nishide, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1200 days.

(21) Appl. No.: 11/619,242

(22) Filed: Jan. 3, 2007

(65) Prior Publication Data

US 2007/0172104 A1    Jul. 26, 2007

(30) Foreign Application Priority Data

Jan. 19, 2006 (JP) ................. 2006-011043

(51) Int. Cl.
*G06K 9/00* (2006.01)
(52) U.S. Cl. .................. 382/131; 382/128
(58) Field of Classification Search .......... 382/128, 382/131
See application file for complete search history.

(56) References Cited

U.S. PATENT DOCUMENTS

| | | | |
|---|---|---|---|
| 5,341,460 A | 8/1994 | Tam | |
| 5,668,846 A | 9/1997 | Fox et al. | |
| 5,928,314 A | 7/1999 | Pelgrom et al. | |
| 6,801,594 B1 | 10/2004 | Ali et al. | |
| 7,054,475 B2 | 5/2006 | Edic et al. | |
| 7,148,903 B2 * | 12/2006 | Brunner et al. | 345/626 |
| 7,602,953 B2 * | 10/2009 | Haider et al. | 382/128 |
| 7,650,023 B2 * | 1/2010 | Fischer et al. | 382/128 |
| 2001/0048731 A1 | 12/2001 | Nakamura et al. | |
| 2006/0204070 A1 | 9/2006 | Hinshaw | |
| 2007/0019851 A1 * | 1/2007 | Nishide et al. | 382/131 |
| 2007/0086560 A1 * | 4/2007 | Kia et al. | 378/7 |

FOREIGN PATENT DOCUMENTS

| | | |
|---|---|---|
| EP | 0 280 412 A2 | 8/1988 |
| EP | 0 506 302 A | 9/1992 |
| EP | 1 081 656 A2 | 3/2001 |
| JP | 11-167622 * | 6/1999 |
| JP | 11 167622 A | 6/1999 |
| JP | 2001 087229 A | 4/2001 |
| JP | 2005-131287 * | 5/2005 |
| JP | 2005131287 | 5/2005 |

OTHER PUBLICATIONS

Johnson G. Allan, et al., "Body Computed Tomography—Image Techniques for Multiplanar Computed Tomography", Sep. 1982, p. 829-834.

(Continued)

*Primary Examiner* — Stephen Koziol
(74) *Attorney, Agent, or Firm* — Armstrong Teasdale LLP

(57) ABSTRACT

The present invention aims to realize an improvement in image quality of a two-dimensional display extracted from a three-dimensional display image such as continuous tomographic images which tomographic images at a conventional scan or the like of an X-ray CT apparatus having a two-dimensional X-ray area detector of a matrix structure typified by a multi-row X-ray detector or a flat panel X-ray detector are arranged in a z direction corresponding to an imaging table travel direction. For the purpose, an image display apparatus of the present invention comprises image filter processing device for preforming a image filter processing on the three-dimensional image, wherein said image filter process varies depending on a cross sectional direction of said two-dimensional image to be displayed.

14 Claims, 25 Drawing Sheets

OTHER PUBLICATIONS

Bovik A Ed: "Handbook of image and video processing, Passage" Handbook of image and video processing, Communications, Networking and Multimedia, San Diego, CA: Academic Press, US, 2000, p. 119-123, XP007902994.

Jiang Hsieh Ed—Hsieh J: "Computed Tomography passage" Computed Tomography : Principles, Design, Artifacts, and Recent Advances, Belligham, WA: Spie, US, 2003, p. 101-111, XP007902993.

International Search Report for Netherlands Application No. 1033252, dated Sep. 25, 2007.

Japan Patent Office, Notice of Reasons for Rejection for Application No. 2006-011043, Oct. 19, 2010, 3 pages.

* cited by examiner

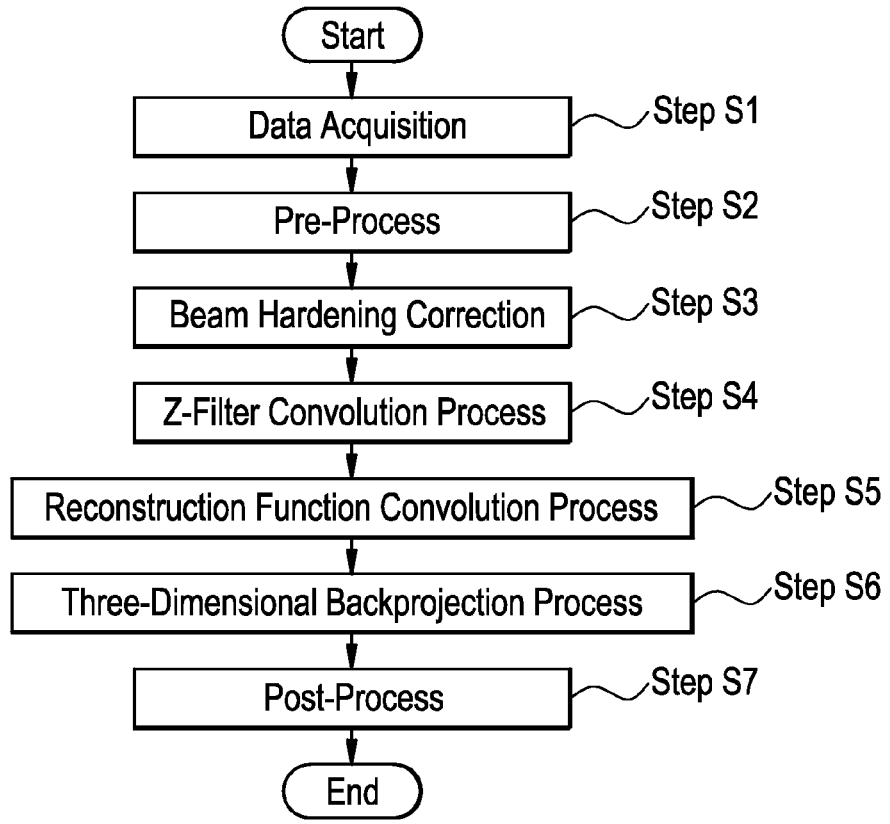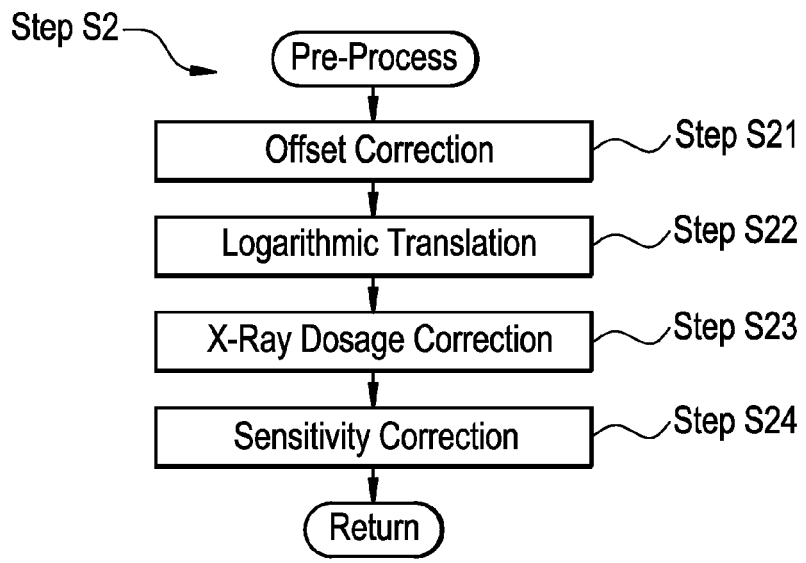

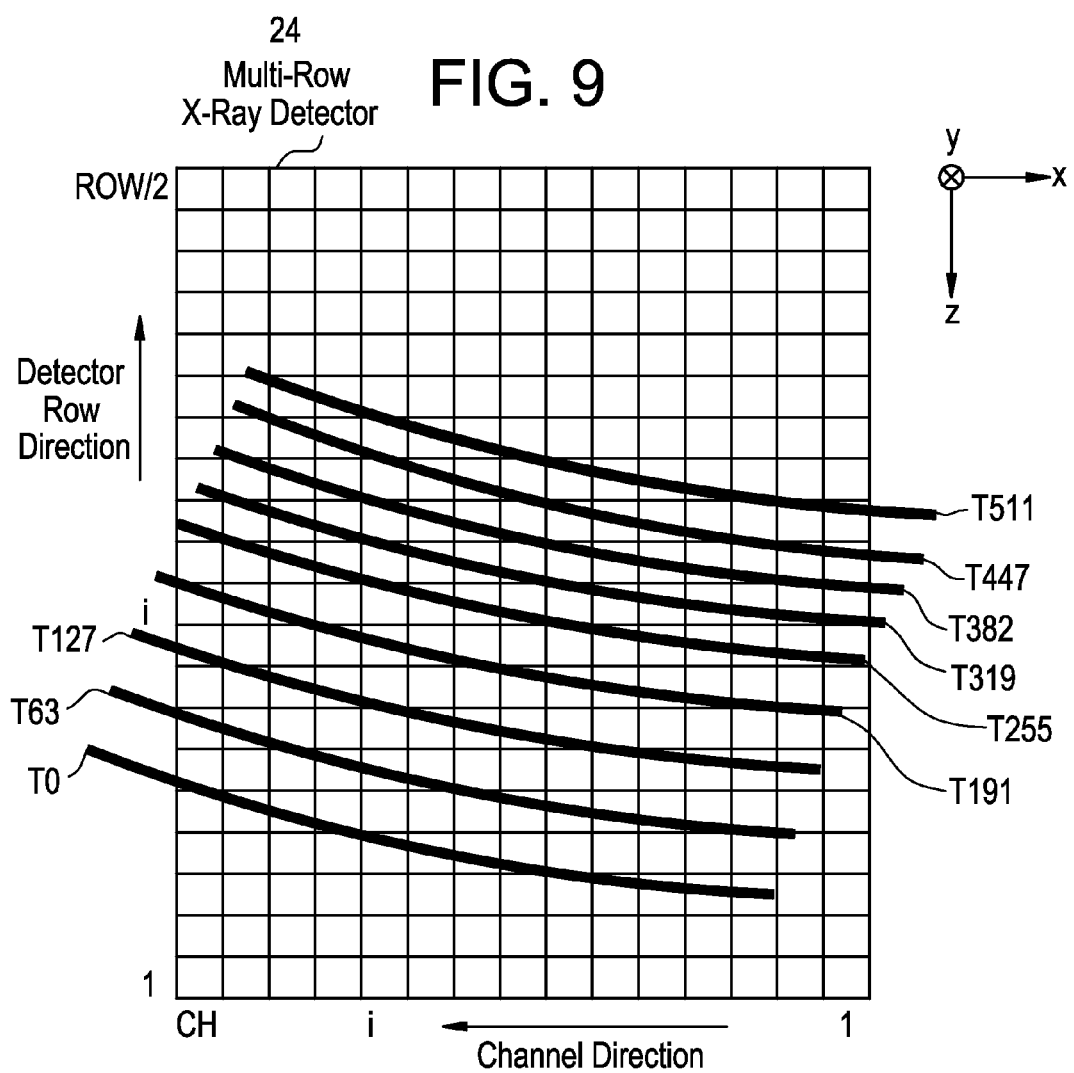

| d | c | d |
|---|---|---|
| c | b | c |
| d | c | d | z=n+1

| c | b | c |
|---|---|---|
| b | a | b |
| c | b | c | z=n

| d | c | d |
|---|---|---|
| c | b | c |
| d | c | d | z=n-1

} Examples of Active Image Filters

| Example 1 | Example 2 | Example 3 |
|---|---|---|
| a=1/27 | a=1/19 | a=1/7 |
| b=1/27 | b=1/19 | b=1/7 |
| c=1/27 | c=1/19 | c=0 |
| d=1/27 | d=0 | d=0 |

Local Noted Pixel Neighbouring Area

Sightline Directions Viewed From 360° Directions

Heart
Lung

Section Transformation Viewed With Being Done in 360° Directions

IMAGE DISPLAY APPARATUS AND X-RAY CT APPARATUS

CROSS REFERENCE TO RELATED APPLICATIONS

This application claims the benefit of Japanese Application No. 2006-011043 filed Jan. 19, 2006.

BACKGROUND OF THE INVENTION

The present invention relates to a medical X-ray CT (Computed Tomography) apparatus or an image display apparatus and an X-ray CT apparatus each of which realizes an improvement in image quality of a three-dimensional image display image comprised of a continuous tomographic image at a conventional scan (called also "axial scan"), a cine scan, a helical scan, a variable-pitch helical scan, or a helical shuttle scan executed in an industrial X-ray CT apparatus.

An MPR (Multi Plane Reformat) display corresponding to one of three-dimensional image display methods has heretofore been effected on a tomographic image continuous in a z-direction corresponding to a table travel direction of an X-ray CT apparatus using a multi-row X-ray detector or an X-ray CT apparatus using a two-dimensional X-ray area detector of a matrix structure typified by a flat panel and an MPR display of an xz plane or an xy plane has been performed as shown in FIG. 15. In this case, a problem arises in that although effects such as an S/N improvement in the xy plane, a reduction in artifact, etc. are brought about when a z-direction adaptive image filter is applied or effected on a tomographic image of the xy plane, spatial resolution is degraded in the z direction and image quality is degraded with respect to an MPR display image of the xz plane or yz.

However, in the X-ray CT apparatus having the multi-row X-ray detector or the X-ray CT apparatus having the two-dimensional X-ray area detector typified by the flat panel, a sheet of tomographic image becomes thin as the cone angle of an X-ray cone beam becomes larger and each detector channel becomes smaller. There is a tendency that S/N of the tomographic image becomes poor on the condition that X ray dosage is constant. However, the X-ray dosage cannot be increased in terms of X-ray exposure of the subject. Therefore, the S/N of each pixel of the thin tomographic image is improved and an adaptive image filter that does not degrade its spatial resolution is determined. On the other hand, each pixel might be observed from various directions of the xy plane, yz plane and xz plane upon the MPR display corresponding to one of the three-dimensional pixel displays. Therefore, when the adaptive image filter is applied in a given fixed direction, degradation of spatial resolution will appear on any of the xy plane, yz plane and xz plane.

Therefore, there is a demand for an adaptive image filter that changes the direction in which it is dynamically applied, following dynamic changes in display and sightline directions. At this time, the adaptive image filter may dynamically be applied in real time upon display.

SUMMARY OF THE INVENTION

With the foregoing in view, an object of the present invention is to provide an image display apparatus and an X-ray CT apparatus each of which is capable of displaying a three-dimensional display image improved in S/N, reduced in artifact and undegraded in spatial resolution even as viewed from any sightline direction upon three-dimensionally displaying a three-dimensional image corresponding to a continuous tomographic image at a conventional scan (axial scan), a cine scan, a helical scan, a variable-pitch helical scan or a helical shuttle scan of an X-ray CT apparatus having a two-dimensional X-ray area detector of a matrix structure typified by a multi-row X-ray detector or a flat panel X-ray detector.

The present invention is provided wherein when a two-dimensional image for displaying a three-dimensional image corresponding to a continuous tomographic image at a conventional scan (axial scan), a cine scan, a helical scan, a variable-pitch helical scan or a helical shuttle scan of an X-ray CT apparatus having a two-dimensional X-ray area detector of a matrix structure typified by a multi-row X-ray detector or a flat panel X-ray detector, on a two-dimensional monitor is created upon three-dimensionally displaying the three-dimensional image, an S/N improvement and a reduction in artifact can be carried out without recognizing degradation in spatial resolution of an image if an image filter or an adaptive image filter is applied in its display direction, its sightline direction or the direction unparallel to its two-dimensional image plane.

Thus, if the adaptive image filter capable of performing an S/N improvement and a reduction in artifact is applied in the direction orthogonal or unparallel to the two-dimensional image for displaying the three-dimensional image on the two-dimensional monitor where a two-dimensional image representing a three-dimensional image like an MPR image is S/N-improved and artifact-reduced, then degradation in spatial resolution is not recognized on the two-dimensional image since such a direction results in the sightline direction, even though the spatial resolution is degraded by the adaptive image filter. Thus, the above problem is solved by providing an image display apparatus and an X-ray CT apparatus characterized in that an S/N improvement and a reduction in artifact can be carried out without degradation of the spatial resolution by dynamically applying the adaptive image filter in consideration of the sightline direction at all times.

In a first aspect, the present invention provides an image display apparatus for displaying a two-dimensional image extracted from a three-dimensional image, comprising image filter processing device for preforming a image filter processing on the three-dimensional image, wherein said image filter process varies depending on a cross sectional direction of said two-dimensional image to be displayed.

In the image display apparatus according to the first aspect, an adaptive image filter or an image filter capable of performing an S/N improvement and a reduction in artifact is applied in the direction in which degradation in spatial resolution is not recognized on the section of the three-dimensional image, according to the display section direction of the three-dimensional image upon the sectional display of the three-dimensional image, thereby making it possible to carry out the S/N improvement and the artifact reduction without degrading the spatial resolution.

In a second aspect, the present invention provides an X-ray CT apparatus comprising X-ray data acquisition device for acquiring X-ray projection data transmitted through a subject existing at a position between an X-ray generator and a two-dimensional X-ray area detector for detecting X-rays in opposition to the X-ray generator, while the X-ray generator and the two-dimensional X-ray area detector are being rotated about the center of rotation corresponding to said position; image reconstructing device for image-reconstructing the projection data acquired from the X-ray data acquisition device; image display device for displaying the image-reconstructed tomographic image; and imaging condition setting device for setting imaging conditions used for execution of said acquisition and said display, wherein the image display device includes image filter processing device for displaying a two-dimensional image extracted from a three-dimensional image constituted of a tomographic image continuous in a z-direction corresponding to the direction of travel of a cradle with the subject placed thereon, wherein said image filter process varies depending on a cross sectional direction of said two-dimensional image to be displayed.

In the X-ray CT apparatus according to the second aspect, any of an image-reconstructed tomographic image or a three-dimensionally displayed image, an MPR-displayed image, an MIP (Maximum Intensity Projection)-displayed image, and a reprojection-displayed image is transformed into a two-dimensional image and displayed on a two-dimensional monitor. That is, a sightline direction relative to the two-dimensional image exists. Degradation in spatial resolution is not recognized visually in the sightline direction. Therefore, an adaptive image filter or an image filter capable of carrying out an S/N improvement and a reduction in artifact is applied in the direction to fail to notice that the spatial resolution has been degraded, thereby to make it possible to carry out the S/N improvement and artifact reduction without degradation in spatial resolution.

In a third aspect, the present invention provides an X-ray CT apparatus wherein in the X-ray CT apparatus according to the second aspect, said image filter process varies image filter coefficients for image filter processing.

In the X-ray CT apparatus according to the third aspect, the image display device adjusts the image filter coefficients in such a manner that an S/N improvement and a reduction in artifact can be effected on an image-reconstructed tomographic image or a three-dimensionally displayed image, an MPR displayed image, an MIP displayed image, and a reprojection-displayed image as viewed in a sightline direction, thereby making it possible to fail to observe degradation in spatial resolution as viewed in the sightline direction.

In a fourth aspect, the present invention provides an X-ray CT apparatus wherein in the X-ray CT apparatus according to the second or third aspect, said image filter processing device preforms the image filter processing in direction orthogonal to the cross sectional direction of said two-dimensional image to be displayed.

In the X-ray CT apparatus according to the fourth aspect, an image-reconstructed tomographic image or a three-dimensionally displayed image, an MPR displayed image, an MIP displayed image and a reprojection-displayed image are transformed into two-dimensional images by the image display device, followed by being displayed on monitors. However, the sightline direction normally corresponds to the direction orthogonal to a monitor display plane, i.e., the direction orthogonal to a two-dimensional image plane displayed on each monitor. Therefore, an adaptive image filter or an image filter capable of performing an S/N improvement and a reduction in artifact is applied in the direction orthogonal to the plane of each of the image-reconstructed tomographic image or the three-dimensionally displayed image, the MPR displayed image, the MIP displayed image and the reprojection-displayed image, thereby to make it possible to carry out the S/N improvement and the artifact reduction without degrading the spatial resolution as viewed from the sightline direction.

In a fifth aspect, the present invention provides an X-ray CT apparatus wherein in the X-ray CT apparatus according to any of the second to fourth aspects, said image filter processing device preforms the image filter processing using an adaptive image filter adapted to image characteristic quantities of a pixel-of-interest subjected to the image filter processing and neighboring pixels adjacent to the pixel-of-interest.

In the X-ray CT apparatus according to the fifth aspect, an image filter is applied to each of an image-reconstructed tomographic image or a three-dimensionally displayed image, an MPR displayed image, an MIP displayed image and reprojection-displayed image as viewed in a sightline direction by the image filter processing device to make spatial resolution appear to undegrade in the sightline direction. When an S/N-improvement and artifact-reduction image filter is applied as viewed in the sightline direction, pixels to which an image filter is applied are selected depending upon image characteristic quantities of a pixel-of-interest for the image filter and its neighboring pixels, whereby the use of an adaptive image filter adapted to the neighboring pixels further restricts degradation in spatial resolution to thereby make it possible to bring about the effects of the S/N improvement and the reduction in artifact.

In a sixth aspect, the present invention provides an X-ray CT apparatus wherein in the X-ray CT apparatus according to the fifth aspect, the image characteristic quantities contain CT values for the pixel-of-interest and the neighboring pixels.

In the X-ray CT apparatus according to the sixth aspect, when an adaptive image filter is applied to each of an image-reconstructed tomographic image or a three-dimensionally displayed image, an MPR displayed image, an MIP displayed image and an reprojection-displayed image as viewed in a sightline direction, pixels to which an image filter is applied are selected according to image characteristic quantities, whereby an adaptive image filter adapted to each of the neighboring pixels is applied. Even though CT values for the pixel-of-interest and its neighboring pixels are used as the image characteristic quantities, effects can sufficiently be brought about.

In a seventh aspect, the present invention provides an X-ray CT apparatus wherein in the X-ray CT apparatus according to the fifth or sixth aspect, the image characteristic quantities contain standard deviations of the CT values for the pixel-of-interest and the neighboring pixels.

In the X-ray CT apparatus according to the seventh aspect, when an adaptive image filter is applied in a sightline direction with respect to each of an image-reconstructed tomographic image or a three-dimensionally displayed image, an MPR displayed image, an MIP displayed image and an reprojection-displayed image, pixels to which an image filter is applied are selected according to image characteristic quantities, whereby an adaptive image filter adapted to each of the neighboring pixels is applied. Even though standard deviations for values of the pixel-of-interest and its neighboring pixels are used as the image characteristic quantities, effects can sufficiently be brought about.

In an eighth aspect, the present invention provides an X-ray CT apparatus wherein in the X-ray CT apparatus according to any one of the second to seventh aspects, the two-dimensional image is an MPR (Multi Plane Reformat) image or an MIP (Maximum Intensity Projection) image.

In the X-ray CT apparatus according to the eighth aspect, a volume rendering three-dimensional display image and an MIP display image both corresponding to other three-dimensional display images, of an image-reconstructed tomographic image or a three-dimensionally displayed image, an MPR displayed image, an MIP displayed image and a reprojection-displayed image are compressed to two-dimensional images and displayed inclusive of information about deep pixels of a three-dimensional image, whereas the image MPR-displayed in particular is a depth-free image obtained by cutting a given plane of a three-dimensional tomographic image corresponding to a continuous tomographic image. Therefore, a sightline direction or the direction orthogonal to a display plane can be definitely determined, and hence the direction to exhibit the effect of an image filter or an adaptive image filter is easy to limit. It is therefore possible to effectively carry out an improvement in S/N and a reduction in artifact without degradation in spatial resolution.

In a ninth aspect, the present invention provides an X-ray CT apparatus wherein in the X-ray CT apparatus according to any one of the second to eighth aspects, the image filter processing device preforms the image filter processing using a three-dimensional image filter.

In the X-ray CT apparatus according to the ninth aspect, when an image-reconstructed tomographic image or a three-dimensionally displayed image, an MPR displayed image, an MIP displayed image and a reprojection-displayed image are displayed on a monitor, the direction orthogonal to the monitor, or a sightline direction can take any direction in three-dimensional space. Therefore, an image filter or an adaptive image filter may also preferably select effective directions freely three-dimensionally. Therefore, if the image filter or the adaptive image filter is of a three-dimensional image filter, then it can adapt to any direction, and an S/N improvement and a reduction in artifact can effectively be carried out without degradation in spatial resolution.

In a tenth aspect, the present invention provides an X-ray CT apparatus wherein in the X-ray CT apparatus according to any one of the second to eighth aspects, the image filter processing device preform the image filter processing using a two-dimensional image filter or a one-dimensional filter.

In the X-ray CT apparatus according to the tenth aspect, when an image-reconstructed tomographic image or a three-dimensionally displayed image, an MPR displayed image, an MIP displayed image and a reprojection-displayed image are displayed on a monitor, the direction orthogonal to the monitor or a sightline direction might be limited to some degree. Therefore, if an image filter or an adaptive image filter are also of a two-dimensional image filter or a one-dimensional filter, then an S/N improvement and a reduction in artifact can be effected without degradation in spatial resolution in the direction orthogonal to each of a three-dimensional display image, an MPR display image and an MIP-processed image displayed on the monitor as two-dimensional images, or in a sightline direction.

In an eleventh aspect, the present invention provides an X-ray CT apparatus wherein in the X-ray CT apparatus according to any one of the second to tenth aspects, the image filter processing device dynamically varies the image filter processing with a change in the cross sectional direction of the image to be displayed while said image is displayed.

In the X-ray CT apparatus according to the eleventh aspect, when a sightline is moved in various directions where an image-reconstructed tomographic image or a three-dimensionally displayed image, an MPR displayed image, an MIP displayed image and a reprojection-displayed image are displayed on a monitor, a sightline direction is tracked and image filter processing is dynamically effected in accordance with the sightline direction at all times, whereby degradation in spatial resolution in the sightline direction by the processing can be set so as to fail to recognize. With such a method, an S/N improvement and a reduction in artifact can be carried out without degradation in spatial resolution.

In an twelfth aspect, the present invention provides an X-ray CT apparatus wherein in the X-ray CT apparatus according to any one of the second to eleventh aspects, the image filter processing device includes optimizing device for optimizing a processing direction of the image filter processing on the three-dimensional image while said image is displayed.

In the X-ray CT apparatus according to the twelfth aspect, when an image-reconstructed tomographic image or a three-dimensionally displayed image, an MPR displayed image, an MIP displayed image and a reprojection-displayed image are displayed on a monitor, the optimum direction always matched with a sightline direction is searched even in the case of a three-dimensional image of a subject rotated in various directions, and a two-dimensional image filter in which an effective direction is matched with the optimum direction can be applied. It is thus possible to carry out an S/N improvement and a reduction in artifact without degradation in spatial resolution.

According to the image display apparatus and X-ray CT apparatus of the present invention, an advantageous effect is brought about which is capable of realizing an X-ray CT apparatus wherein when a three-dimensional image corresponding to a continuous tomographic image at a conventional scan (axial scan), a cine scan, a helical scan, a variable-pitch scan or a helical shuttle scan of an X-ray Ct apparatus having a two-dimensional X-ray area detector of a matrix structure typified by a multi-row X-ray detector or a flat panel X-ray detector is three-dimensionally displayed, S/N is improved as viewed from any sightline direction, artifacts are reduced and a three-dimensional display image free of degradation in spatial resolution can be displayed.

BRIEF DESCRIPTION OF THE DRAWINGS

FIG. 5 is a flow chart showing a schematic operation for image reconstruction, of the X-ray CT apparatus according to the one embodiment of the present invention.

FIG. 6 is a flow chart illustrating the details of a pre-process.

FIG. 9 is a conceptual diagram illustrating lines projected onto an X-ray detector surface.

DETAILED DESCRIPTION OF THE INVENTION

The present invention will hereinafter be explained in further detail by embodiments illustrated in the figures. Incidentally, the present invention is not limited to or by the embodiments.

Figure 1:
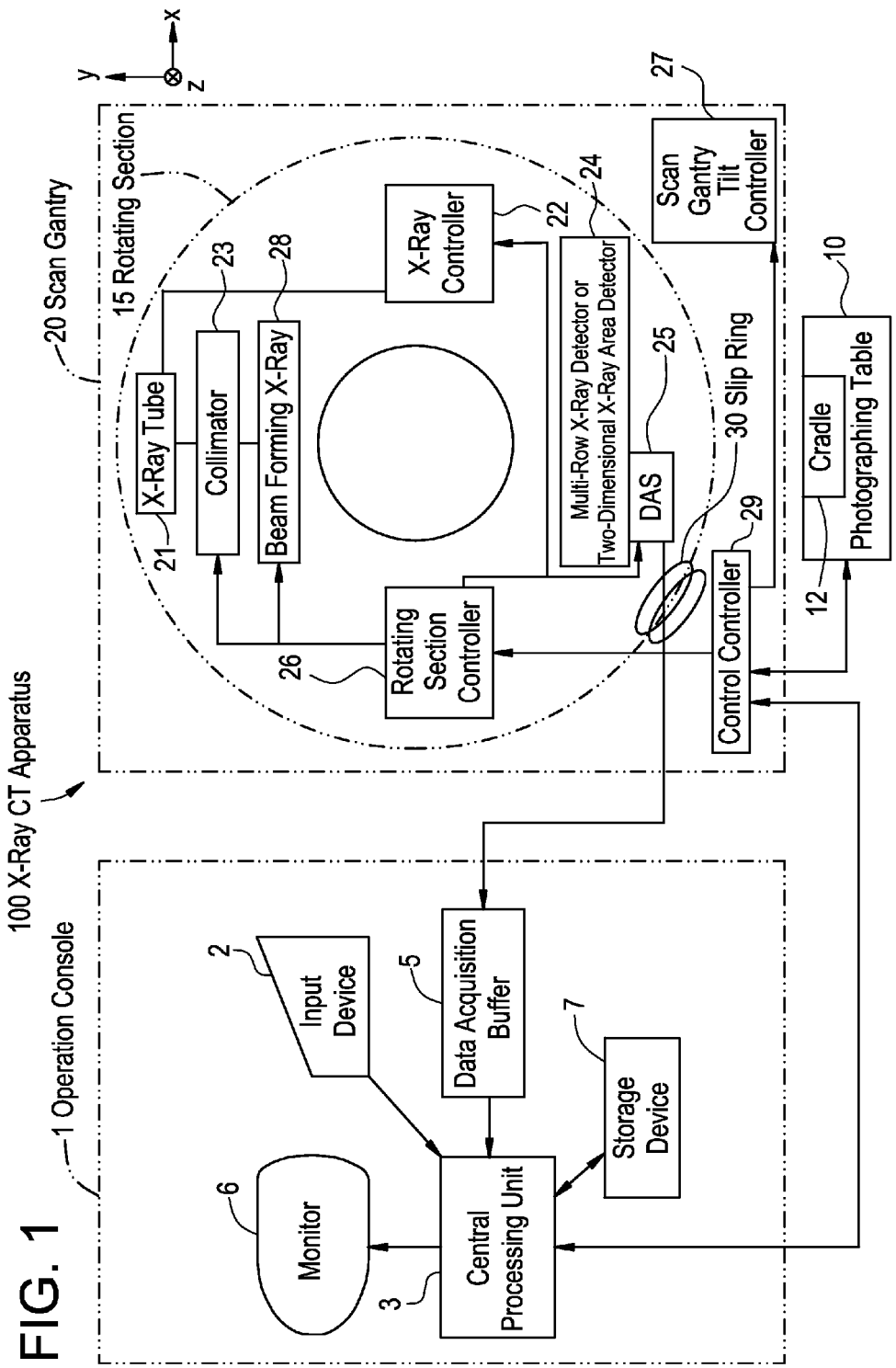
FIG. 1 is a block diagram showing an X-ray CT apparatus according to one embodiment of the present invention.

FIG. 1 is a configuration block diagram showing an X-ray CT apparatus according to one embodiment of the present invention. The X-ray CT apparatus 100 is equipped with an operation console 1, an imaging or photographing table 10 and a scan gantry 20.

The operation console 1 includes an input device 2 which forms or constitutes an image display unit or device and corresponds to imaging condition setting device for accepting an input from an operator, a central processing unit 3 including image reconstructing device which executes a pre-process, an image reconstructing process, a post-process, etc. and image filter processing device, a data acquisition buffer 5 which acquires or collects X-ray detector data acquired by the scan gantry 20, a monitor 6 which displays a tomographic image image-reconstructed from projection data obtained by pre-processing the X-ray detector data, and a storage device 7 which stores programs, X-ray detector data, projection data, projection data and X-ray tomographic images therein.

Figure 14:
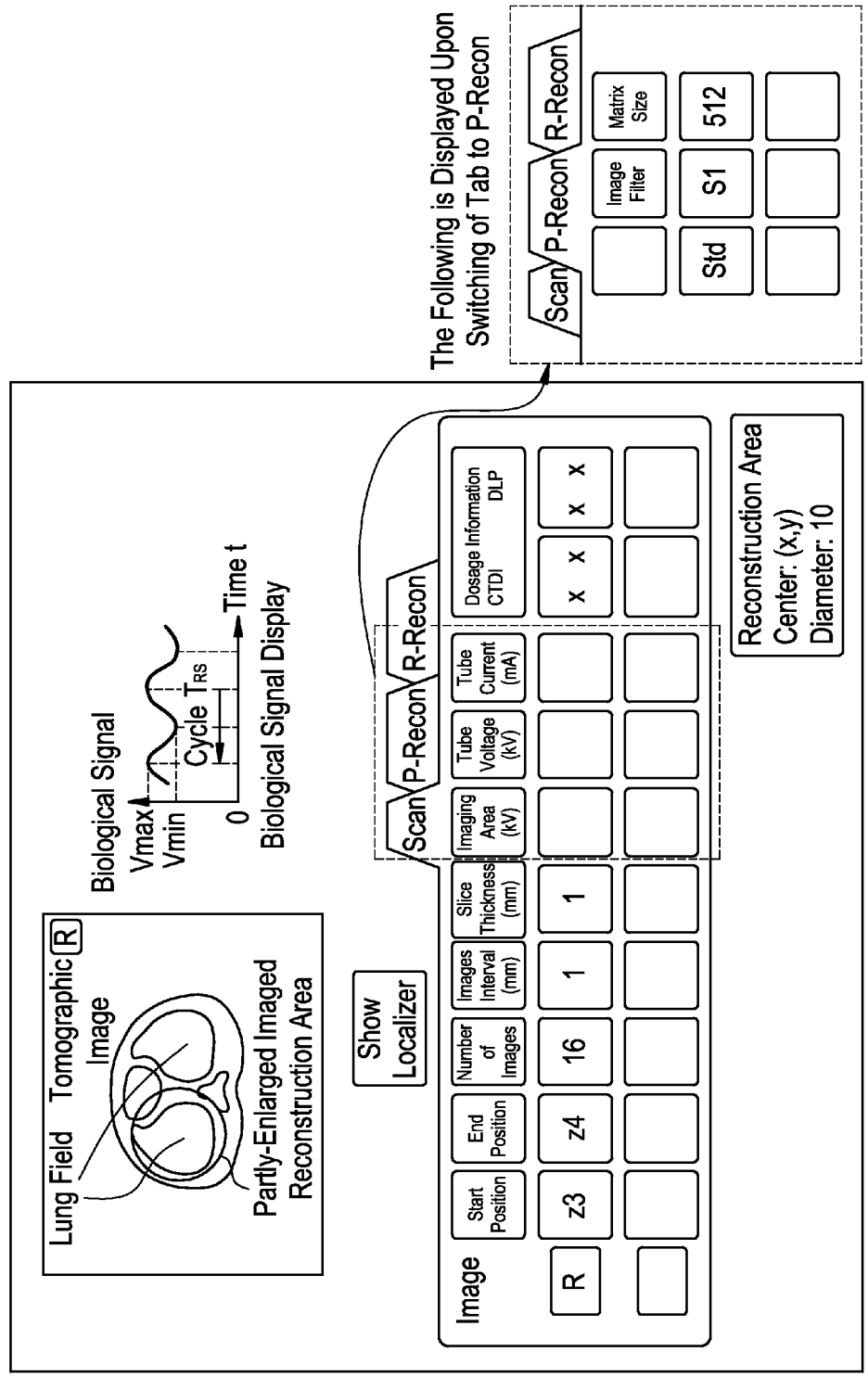
FIG. 14 is an explanatory diagram showing an imaging condition input screen of the X-ray CT apparatus.
Figure 15:
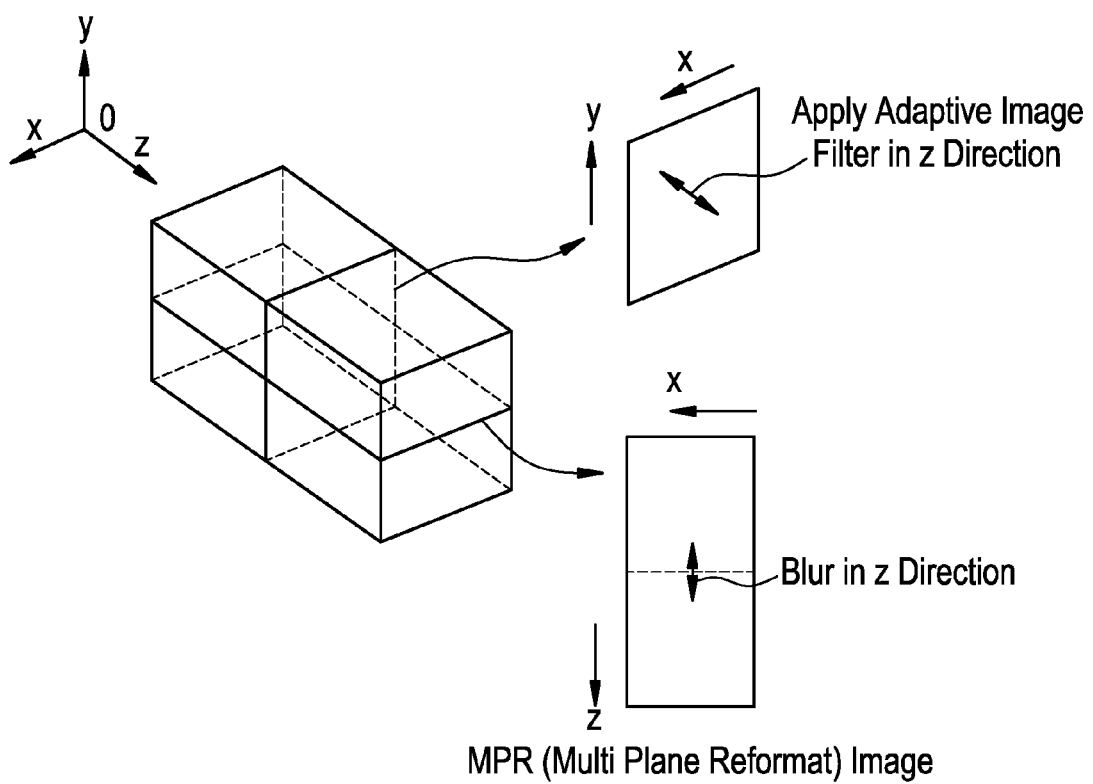
FIG. 15 is an explanatory diagram illustrating z-direction blurring in an MPR image of an xz plane by a z-direction adaptive image filter.

An input for imaging or photographing conditions is inputted from the input device 2 corresponding to the imaging condition setting device and stored in the storage device 7. An example of an imaging condition input screen is shown in FIG. 14.

The photographing table 10 includes a cradle 12 which inserts and draws a subject into and from a bore or aperture of the scan gantry 20 with the subject placed thereon. The cradle 12 is elevated and moved linearly on the photographing table 10 by a motor built in the photographing table 10.

The scan gantry 20 includes an X-ray tube 21 corresponding to an X-ray generator, an X-ray controller 22, a collimator 23, a beam forming X-ray filter 28, a multi-row X-ray detector 24, a DAS (Data Acquisition System) 25. The X-ray tube 21, collimator 23, X-ray detector 24, DAS 25, and the rotating section controller 26 are mounted on a rotating section 15 of the scan gantry 10. A rotating section controller 26, which controls the X-ray tube 21 or the like rotated about a body axis of the subject, and a control controller 29 which swaps control signals or the like with the operation console 1 and the photographing table 10. Here, the X-ray controller 22, DAS 25, rotating section controller 26 and control controller 29 constitute X-ray data acquisition device.

The beam forming X-ray filter 28 is of an X-ray filter configured so as to be thinnest in thickness as viewed in the direction of X rays directed to the center of rotation corresponding to the center of imaging, to increase in thickness toward its peripheral portion and to be able to further absorb the X rays. Therefore, the body surface of a subject whose sectional shape is nearly circular or elliptic can be less exposed to radiation. The scan gantry 20 can be tiled about ±30° or so forward and rearward as viewed in the z direction by a scan gantry tilt controller 27.

The X-ray tube 21 corresponding to the X-ray generator and the multi-row X-ray detector 24 are rotated about the center of rotation IC. Assuming that the vertical direction is a y direction, the horizontal direction is an x direction and the travel direction of the table and cradle orthogonal to these is a z direction, the plane at which the X-ray tube 21 and the multi-row X-ray detector 24 are rotated, is an xy plane. The direction in which the cradle 12 is moved, corresponds to the z direction.

Figure 2:
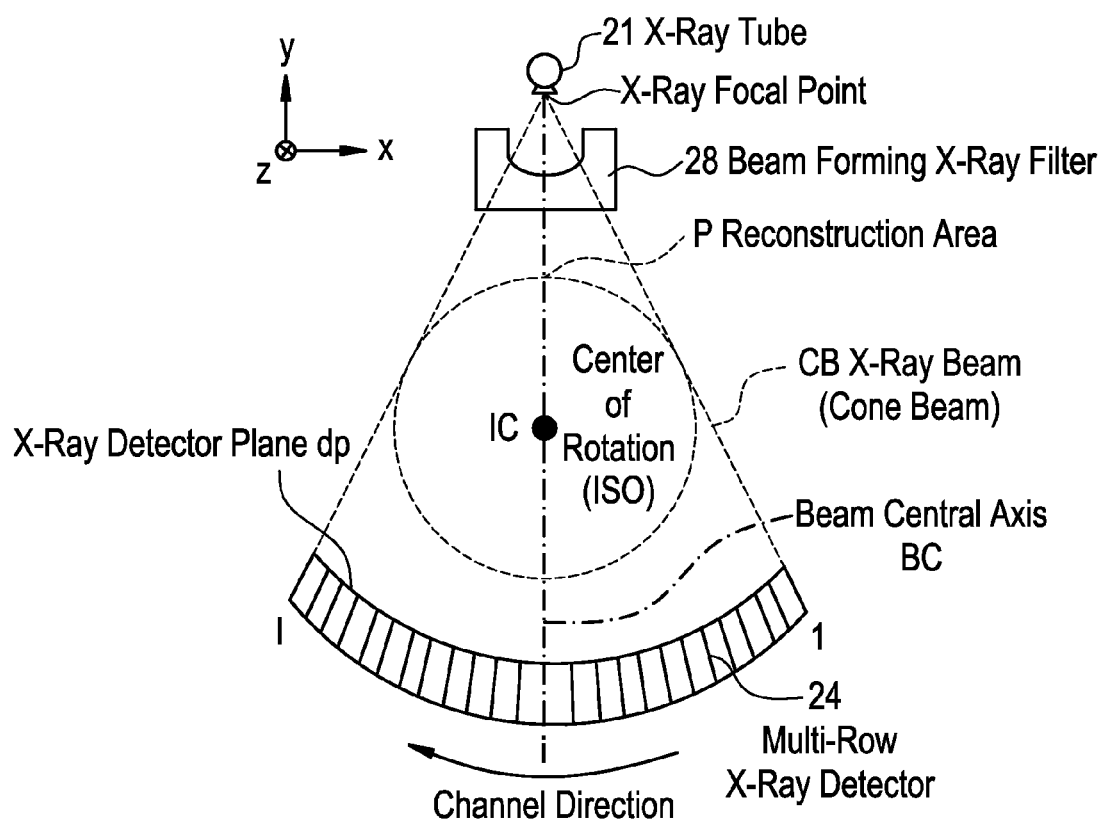
FIG. 2 is an explanatory diagram showing an X-ray generator (X-ray tube) and a multi-row X-ray detector as viewed in an xy plane.
Figure 3:
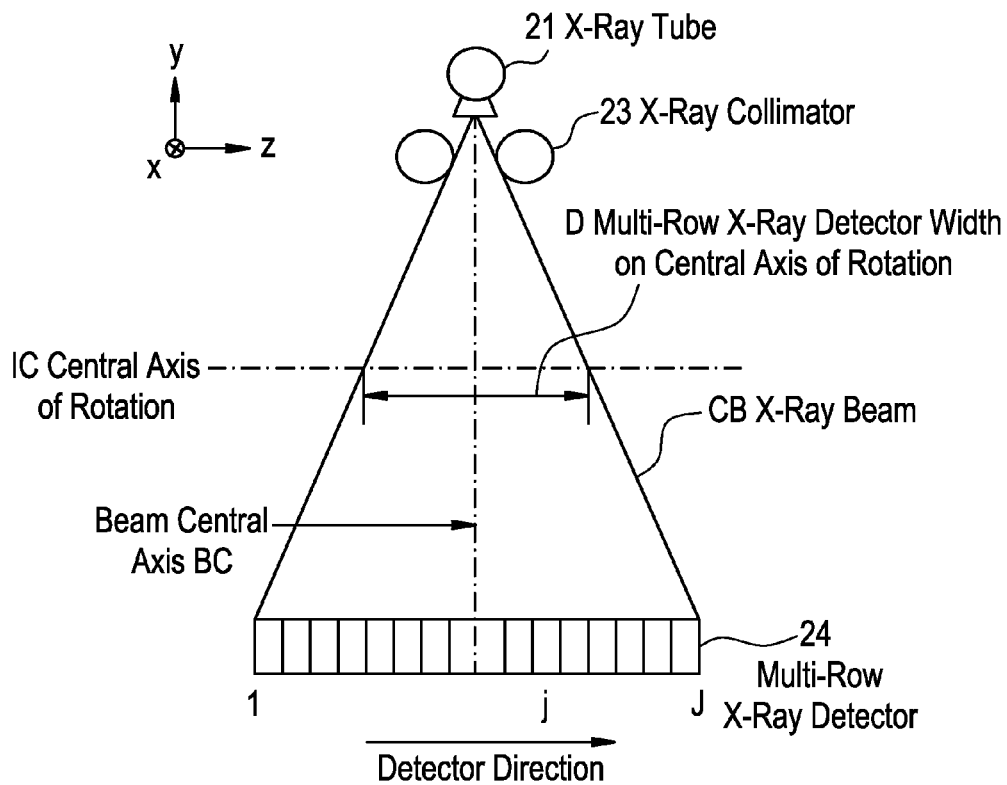
FIG. 3 is an explanatory diagram illustrating the X-ray generator (X-ray tube) and the multi-row X-ray detector as viewed in a yz plane.

FIGS. 2 and 3 are explanatory diagrams showing a geometrical arrangement or layout of the X-ray tube 21 and the multi-row X-ray detector 24 as viewed from the xy plane or yz plane. The X-ray tube 21 generates an X-ray beam called a cone beam CB. When the direction of a central axis of the cone beam CB is parallel to the y direction, this is defined as a view angle 0°.

The multi-row X-ray detector 24 has X-ray detector rows corresponding to, for example, 256 rows as viewed in the z direction. Each of the X-ray detector rows has X-ray detector channels corresponding to, for example, 1024 channels as viewed in a channel direction.

In FIG. 2, the X-ray beam emitted from the X-ray focal point of the X-ray tube 21 is spatially controlled in X-ray dosage by the beam forming X-ray filter 28 in such a manner that more X rays are radiated in the center of a reconstruction area or plane P and less X rays are radiated at a peripheral portion of the reconstruction area P. Thereafter, the X rays are absorbed by the subject that exists inside the reconstruction area P, and the transmitted X rays are acquired by the multi-row X-ray detector 24 as X-ray detector data.

In FIG. 3, the X-ray beam emitted from the X-ray focal point of the X-ray tube 21 is controlled in the direction of a slice thickness of a tomographic image by the collimator 23, that is, the X-ray beam is controlled in such a manner that the width of the X-ray beam becomes D at a central axis of rotation IC. Thus, the X rays are absorbed into the subject existing in the vicinity of the central axis of rotation IC, and the transmitted X rays are acquired by the multi-row X-ray detector 24 as X-ray detector data.

The X-rays are applied and the acquired projection data are A/D converted by the DAS 25 from the multi-row X-ray detector 24, which in turn are inputted to the data acquisition buffer 5 via a slip ring 30. The data inputted to the data acquisition buffer 5 are processed by the central processing unit 3 constituting the image reconstructing device in accordance with the corresponding program stored in the storage device 7, so that the data are image-reconstructed as a tomographic image, followed by being displayed on the monitor 6. Incidentally, the central processing unit 3 also includes the image filter processing device and performs image filter processing to be described later too.

Figure 4:
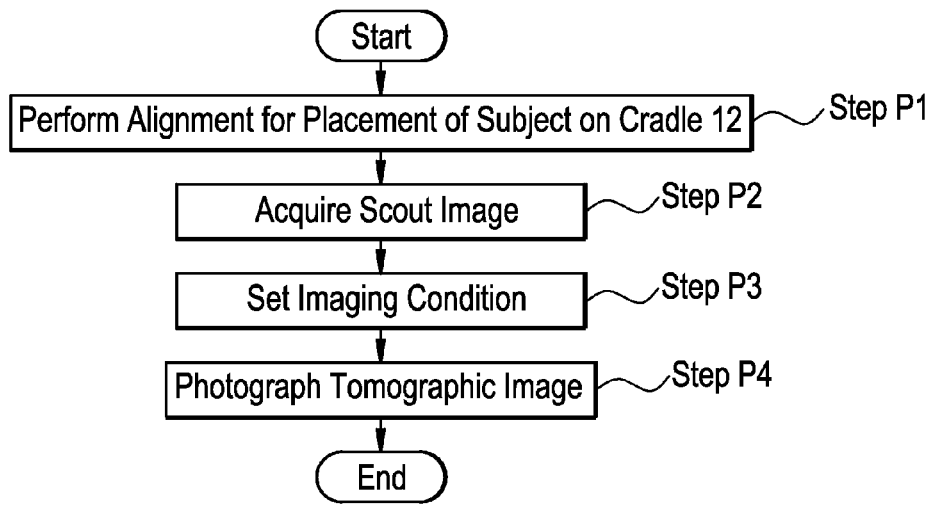
FIG. 4 is a flow chart depicting the flow of subject imaging.

FIG. 4 is a flow chart showing the outline of the operation of the X-ray CT apparatus according to the present embodiment.

At Step P1, the subject is placed on the cradle 12 and its alignment is made. In the subject placed on the cradle 12, a slice light center position of the scan gantry 20 is aligned with a reference point of each region of the subject.

At Step P2, scout image acquisition is performed. While a scout image is normally photographed at 0° and 90°, only a 90° scout image might be photographed or imaged as in the case of, for example, the head, depending upon each region. The details of the photographing of the scout image will be described later.

At Step P3, an imaging or photographing condition is set. As the imaging condition, imaging is normally carried out while the position and size of a tomographic image to be photographed are being displayed on a scout image. In this case, the whole X-ray dosage information corresponding to one helical scan, variable-pitch helical scan, helical shuttle scan, conventional scan (axial scan) or cine scan is displayed. When the number of rotations or time is inputted, X-ray dosage information corresponding to the number of rotations inputted in its area of interest or the time inputted is displayed upon the cine scan.

At Step P4, tomographic image photography is performed. The details of the tomographic image photography will be described in detail later.

FIG. 5 is a flow chart schematically showing the operations for the tomographic image photography and scout image photography, of the X-ray CT apparatus 100 of the present invention.

At Step S1, the operation of rotating the X-ray tube 21 and the multi-row X-ray detector 24 about the subject and effecting data acquisition of X-ray detector data on the cradle 12 placed on the imaging or photographing table 10 while the table is being linearly moved, is performed upon a helical scan. Then, data acquisition in a constant-speed range is performed upon a helical scan for adding a table linear movement z-direction position Ztable(view) to X-ray detector data D0 (view, j, i) indicated by a view angle view, a detector row number j and a channel number i and acquiring the X-ray detector data.

Upon a variable-pitch helical scan or a helical shuttle scan, data acquisition is assumed to be performed even at acceleration and deceleration in addition to the data acquisition in the constant-speed range.

Upon a conventional scan (axial scan) or a cine scan, the data acquisition system is rotated once or plural times while the cradle 12 placed on the photographing table 10 is being fixed to a given z-direction position, thereby to perform data acquisition of X-ray detector data. The cradle 12 is moved to the next z-direction position as needed and thereafter the data acquisition system is rotated once or plural times again to perform data acquisition of X-ray detector data. Upon the scout image photography, the operation of fixing the X-ray tube 21 and the multi-row X-ray detector 24 and performing data acquisition of X-ray detector data while the cradle 12 placed on the photographing table 10 is being linearly moved is performed.

At Step S2, a pre-process is performed on the X-ray detector data D0 (view, j, i) to convert it into projection data. As shown in FIG. 6, the pre-process comprises a Step S21 offset correction, Step S22 logarithmic translation, a Step S23 X-ray dosage correction and a Step S24 sensitivity correction.

If the pre-processed X-ray detector data is displayed upon the scout image photography with each of a pixel size in the channel direction and a pixel size in the z direction corresponding to the cradle linear moving direction being made coincident with a display pixel size of the monitor 6, then the X-ray detector data is completed as the corresponding scout image.

At Step S3, a beam hardening correction is effected on the pre-processed projection data D1 (view, j, i). Assuming that upon the beam hardening correction of Step S3, projection data subjected to the sensitivity correction S24 at the pre-process S2 is defined as D1 (view, j, i) and data subsequent to the beam hardening correction of Step S3 is defined as D11 (view, j, i), the beam hardening correction of Step S3 is expressed in the form of, for example, a polynomial as given by the following equation (1).

[Equation 1]

$$D11(view,j,i) = D1(view,j,i) \cdot (B_0(j,i) + B_1(j,i) \cdot D1(view,j,i) + B_2(j,i) \cdot D1(view,j,i)^2) \quad (1)$$

Since, at this time, the independent beam hardening corrections can be carried out for every j row of the detectors, the difference between X-ray energy characteristics of the detectors placed for every row can be corrected if tube voltages of respective data acquisition systems are different on the imaging condition.

At Step S4, a z-filter convolution process for applying filters in the z direction (row direction) is effected on the projection data D11 (view, j, i) subjected to the beam hardening correction. That is, after the pre-process at each view angle and each data acquisition system, projection data of the multi-row X-ray detector D11 (view, j, i) (where i=1 to CH and j=1 to ROW) subjected to the beam hardening correction is multiplied in the row direction by filters in which such row-direction filter sizes as expressed in the following equations (2) and (3) are five rows, for example.

[Equation 2]

$$(w_1(i), w_2(i), w_3(i), w_4(i), w_5(i)) \quad (2)$$

where
[Equation 3]

$$\sum_{k=1}^{5} w_k(i) = 1 \quad (3)$$

The corrected detector data D12 (view, j, i) is given as expressed in the following equation (4):
[Equation 4]

$$D12(\text{view}, j, i) = \sum_{k=1}^{5} (D11(\text{view}, j+k-3, i) \cdot w_k(j)) \quad (4)$$

Incidentally, assuming that the maximum value of the channel is CH and the maximum value of the row is ROW, the following equations (5) and (6) are established.

[Equation 5]

$$D11(\text{view},-1,i)=D11(\text{view},0,i)=D11(\text{view},1,i) \quad (5)$$

[Equation 6]

$$D11(\text{viw},\text{ROW},i)=D11(\text{view},\text{ROW}+1,i)=D11(\text{view},\text{ROW}+2,i) \quad (6)$$

When row-direction filter coefficients are changed for every channel, slice thicknesses can be controlled depending upon the distance from an image reconstruction center. In a tomographic image, its peripheral portion generally becomes thicker in slice thickness than the reconstruction center thereof. Therefore, when the row-direction filter coefficients are changed at the central and peripheral portions, and the row-direction filter coefficients are widely changed in width in the neighborhood of a central channel and narrowly changed in width in the neighborhood of a peripheral channel, the slice thicknesses can also be made close to each other uniformly even at the peripheral portion and the image reconstruction center.

Controlling the row-direction filter coefficients at the central and peripheral channels of the multi-row X-ray detector 24 in this way makes it possible to control even the slice thicknesses at the central and peripheral portions. Thickening the slice thickness slightly by each row-direction filter yields extensive improvements in both artifact and noise. Thus, the degree of the improvement in artifact and the degree of the improvement in noise can also be controlled. That is, it is possible to control a three-dimensionally image-reconstructed CT or tomographic image, i.e., image quality in the xy plane. As other embodiment, a tomographic image having a thin slice thickness can also be realized by setting row-direction (z-direction) filter coefficients to deconvolution filters.

At Step S5, a reconstruction function convolution process is performed. That is, projection data is subjected to Fourier transformation and multiplied by a reconstruction function, followed by being subjected to inverse Fourier transformation. Assuming that upon the reconstruction function convolution process S5, data subsequent to the z filter convolution process is defined as D12, data subsequent to the reconstruction function convolution process is defined as D13, and the convoluting reconstruction function is defined as Kernel(j), the reconstruction function convolution process is expressed as given by the following equation (7):

[Equation 7]

$$D13(\text{view},j,i)=D12(\text{view},j,i)*\text{Kernel}(j) \quad (7)$$

That is, since the independent reconstruction function convolution process can be performed for every j row of the detectors, the reconstruction function Kernel (j) can correct differences in noise characteristic and spatial resolution characteristic for every row.

At Step S6, a three-dimensional backprojection process is effected on the projection data D13 (view, j, i) subjected to the reconstruction function convolution process to determine backprojection data D3 (x, y, z). An image-reconstructed image is three-dimensionally image-reconstructed on a plane, i.e., an xy plane orthogonal to the z axis. A reconstruction area or plane P to be shown below is assumed to be parallel to the xy plane. The three-dimensional backprojection process will be explained later referring to FIG. 5.

At Step S7, a post-process including image filter convolution, CT value conversion and the like is effected on the backprojection data D3 (x, y, z) to obtain a CT or tomographic image D31 (x, y). Assuming that upon the image filter convolution process in the post-process, a tomographic image subsequent to the three-dimensional backprojection is defined as D31 (x, y, z), data subsequent to the image filter convolution is defined as D32 (x, y, z), and a two-dimensional image filter convolved on the xy plane corresponding to a tomographic image plane is defined as Filter(z), the following equation (8) is established.

[Equation 8]

$$D32(x,y,z)=D31(x,y,z)*\text{Filter}(z) \quad (8)$$

That is, since the independent image filter convolution process can be performed for every j row of the detectors, it is possible to correct differences in noise characteristic and spatial resolution characteristic for every row. Alternatively, an image space z-direction filter convolution process shown below may be performed after the two-dimensional image filter convolution process. The image space z-direction filter convolution process may be performed before the two-dimensional image filter convolution process. Further, a three-dimensional image filter convolution process may be performed to bring about such an effect as to share both the two-dimensional image filter convolution process and the image space z-direction filter convolution process.

Assuming that upon the image space z-direction filter convolution process, a tomographic image subjected to the image space z-direction filter convolution process is defined as D33 (x, y, z), and a tomographic image subjected to the two-dimensional image filter convolution process is defined as D32 (x, y, z), the following relation is established:

[Equation 9]

$$D32(x, y, z) = \sum_{i=-l}^{l} D32(x, y, z+i) \cdot v(i) \quad (9)$$

where v(i) becomes the following coefficient row in the form of image space z-direction filter coefficients at which the width in the z direction is 2l+1.

[Equation 10]

$$v(-l), v(-/+l+1), \ldots v(-1), v(0), v(1), \ldots v(l-1), v(l) \quad (10)$$

Upon the helical scan, the image space filter coefficient v(i) may be an image space z-direction filter coefficient independent on a z-direction position. However, when the two-dimensional X-ray area detector or the multi-row X-ray detector 24 broad in detector width as viewed in the z direction is used in particular, the image space z-direction filter coefficient v(i) can be subjected to detailed adjustments dependent on row positions of respective tomographic images upon the conventional scan (axial scan) or the cine scan if the image space z-direction filter coefficient v(i) is given as each of image space z-direction filter coefficients dependent on the positions of the rows of the X-ray detector in the z direction. Therefore, this is further effective. The resultant tomographic images are displayed on the monitor 6.

Figure 7:
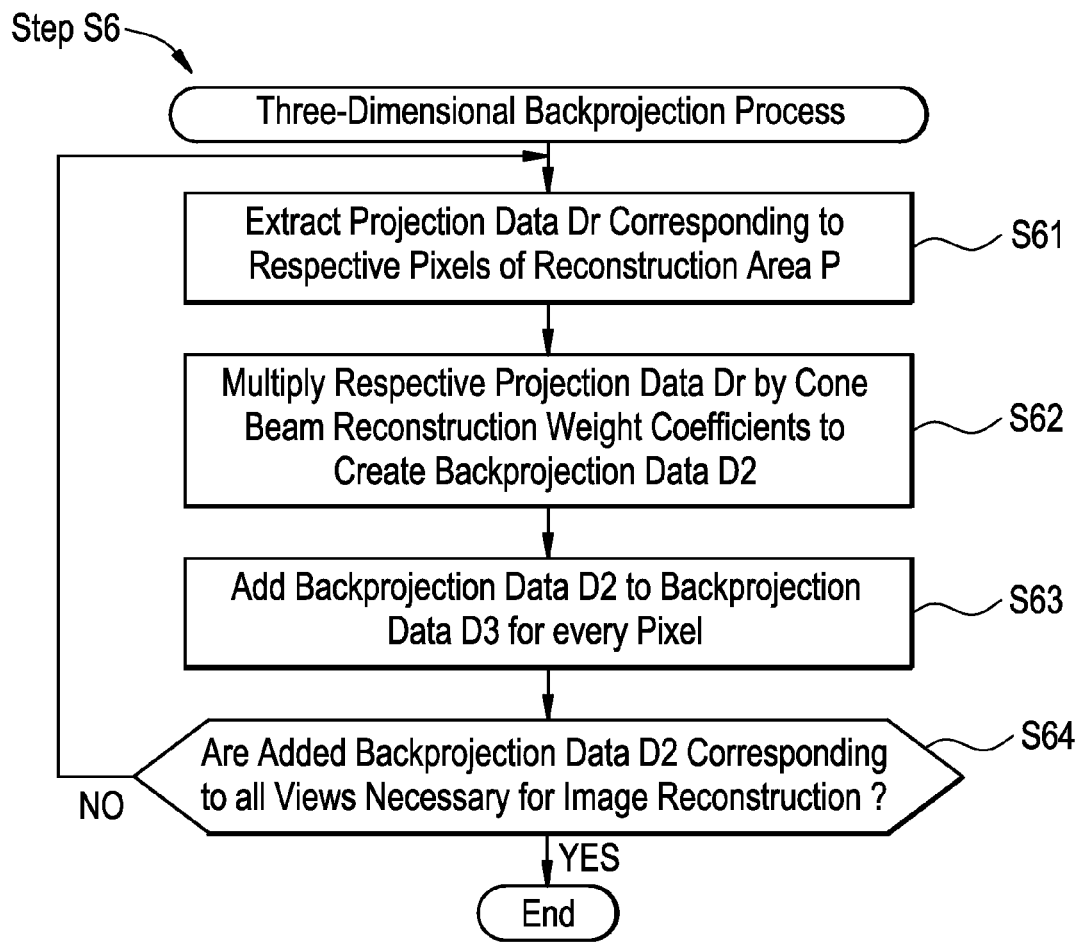
FIG. 7 is a flow chart depicting the details of a three-dimensional image reconstructing process.

FIG. 7 is a flow chart showing the details of the three-dimensional backprojection process (Step S6 in FIG. 5). In the present embodiment, an image to be image-reconstructed is three-dimensionally image-reconstructed on an xy plane corresponding to a plane orthogonal to the z axis. The following reconstruction area P is assumed to be parallel to the xy plane.

At Step S61, attention is given to one of all views (i.e., views corresponding to 360° or views corresponding to "180°+fan angles") necessary for image reconstruction of a tomographic image. Projection data Dr corresponding to respective pixels in a reconstruction area P are extracted.

Figure 8A:
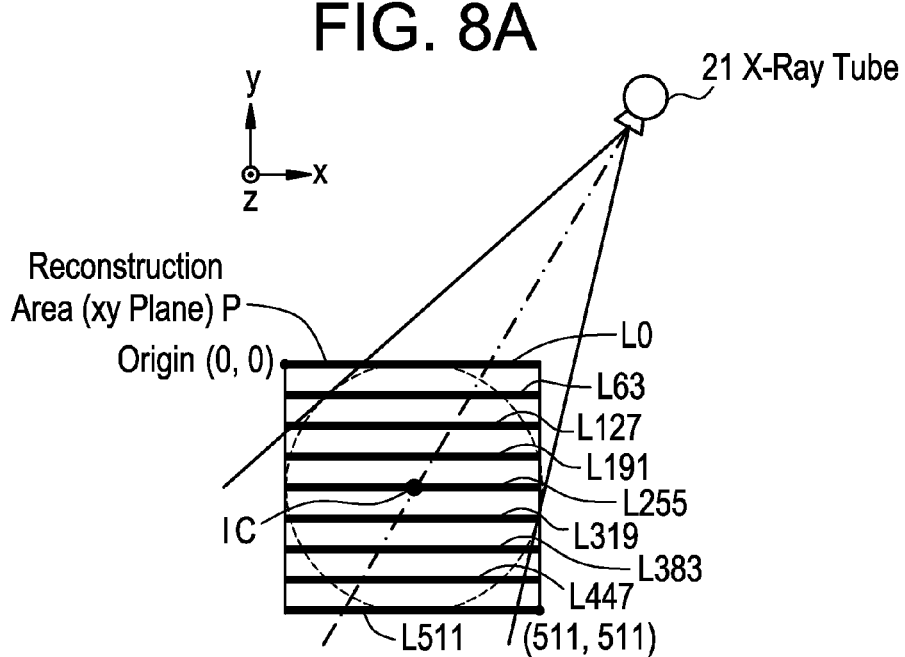
FIGS. 8a and 8b are conceptual diagrams showing a state in which lines on a reconstruction area are projected in an X-ray penetration direction.
Figure 8B:
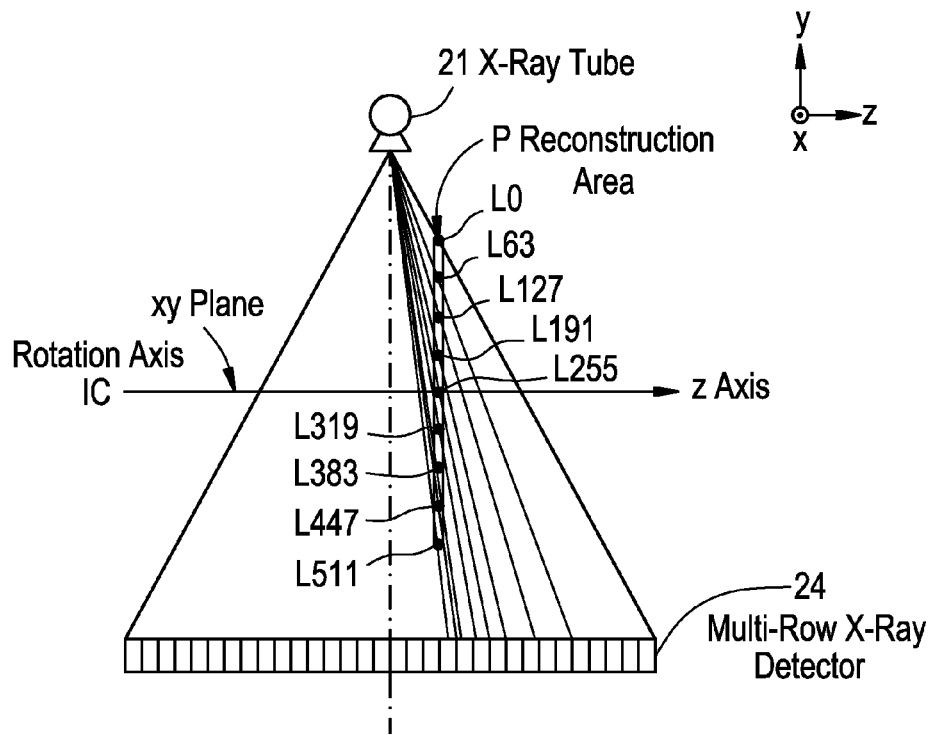

As shown in FIGS. 8(a) and 8(b), a square area of 512×512 pixels, which is parallel to the xy plane, is assumed to be a reconstruction area P. Further, a pixel row L0 parallel to an x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=447, and a pixel row L511 of y=511 are taken for example. If projection data on lines T0 through T511 obtained by projecting these pixel rows L0 to L511 on the plane of the multi-row X-ray detector 24 in an X-ray penetration direction are extracted as shown in FIG. 9, then they result in projection data Dr (view, x, y) of the pixel rows L0 to L511. However, x and y correspond to respective pixels (x, y) of the tomographic image.

The X-ray penetration direction is determined depending on geometrical positions of the X-ray focal point of the X-ray tube 21, the respective pixels and the multi-row X-ray detector 24. Since, however, the z coordinates z(view) of X-ray detector data D0 (view, j, i) are known with being added to X-ray detector data as a table linear movement z-direction position Ztable(view), the X-ray penetration direction can be accurately determined within the X-ray focal point and the data acquisition geometrical system of the multi-row X-ray detector even in the case of the X-ray detector data D0 (view, j, i) placed under acceleration and deceleration.

Figure 10:
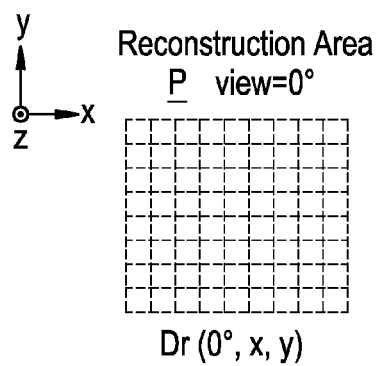
FIG. 10 is a conceptual diagram showing a state in which projection data Dr (view, x, y) are projected onto a reconstruction area.

Incidentally, when some of lines are placed out of the multi-row X-ray detector 24 as viewed in the channel direction as in the case of, for example, the line T0 obtained by projecting, for example, the pixel row L0 on the plane of the multi-row X-ray detector 24 in the X-ray penetration direction, the corresponding projection data Dr (view, x, y) is set to "0". When it is placed outside the multi-row X-ray detector 24 as viewed in the z direction, the corresponding projection data Dr (view, x, y) is determined by extrapolation. Thus, as shown in FIG. 10, the projection data Dr (view, x, y) corresponding to the respective pixels of the reconstruction area P can be extracted.

Figure 11:
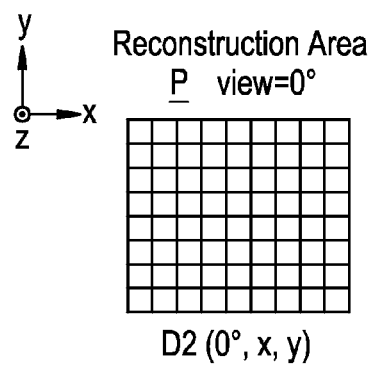
FIG. 11 is a conceptual diagram showing backprojection pixel data D2 corresponding to respective pixels on a reconstruction area.

Referring back to FIG. 7, at Step S62, the projection data Dr (view, x, y) are multiplied by a cone beam reconstruction weight coefficient to create projection data D2 (view, x, y) as shown in FIG. 11. Now, the cone beam reconstruction weight function w (i, j) is as follows. Generally, when the angle which a linear line connecting the focal point of the X-ray tube 21 and a pixel g(x, y) on the reconstruction area P (xy plane) at view=βa forms with a center axis Bc of an X-ray beam is assumed to be γ and its opposite view is assumed to be view=βb in the case of fan beam image reconstruction, their relations are expressed as given by the following equation (11).

[Equation 11]

$$\beta b = \beta a + 180° - 2\gamma \quad (11)$$

When the angles which the X-ray beam passing through the pixel g(x, y) on the reconstruction area P and its opposite X-ray beam form with the reconstruction plane P, are assumed to be αa and αb respectively, they are multiplied by cone beam reconstruction weight coefficients ωa and ωb dependant on these and added together to determine backprojection pixel data D2 (0, x, y). In this case, it is given as expressed in the following equation (12)

[Equation 12]

$$D2(0,x,y) = \omega a \cdot D2(0,x,y)\_a + \omega b \cdot D2(0,x,y)\_b \quad (12)$$

where D2(0,x,y)_a: backprojection data of view βa
D2(0,x,y)_b is assumed to be backprojection data of view βb.

Incidentally, the sum of the cone beam reconstruction weight coefficients corresponding to the beams opposite to each other is expressed like the following equation (13):

[Equation 13]

$$\omega a + \omega b = 1 \quad (13)$$

The above addition with multiplication of the cone beam reconstruction weight coefficients ωa and ωb enables a reduction in cone angle artifact. For example, ones determined by the following equations can be used as the cone beam reconstruction weight coefficients ωa and ωb. Incidentally, ga indicates the weight coefficient of the view βa and gb indicates the weight coefficient of the view βb.

When ½ of a fan beam angle is assumed to be γmax, the following relations are established as given by the following equations (14) to (19):

[Equation 14]

$$ga = f(\gamma \max, \alpha a, \beta a) \quad (14)$$

[Equation 15]

$$gb = f(\gamma \max, \alpha b, \beta b) \quad (15)$$

[Equation 16]

$$xa = 2 \cdot ga^q / (ga^q + gb^q) \quad (16)$$

[Equation 17]

$$xb=2 \cdot gb^q/(ga^q+gb^q) \quad (17)$$

[Equation 18]

$$wa=xa^2 \cdot (3-2xa) \quad (18)$$

[Equation 19]

$$wb=xb^2 \cdot (3-2xb) \quad (19)$$

(where, for example, q=1).

Assuming that max are defined as functions which adopt or take larger values as examples of ga and gb, for example, ga an gb are given as expressed in the following equations (20) and (21).

[Equation 20]

$$ga=\max[0,\{(\pi/2+\gamma \max)-|\beta a|\}\cdot|\tan(\alpha a))| \quad (20)$$

[Equation 21]

$$gb=\max [0,\{(\pi/2+\gamma \max)-|\beta b|\}\cdot|\tan(\alpha b))| \quad (21)$$

In the case of the fan beam image reconstruction, each pixel on the reconstruction area P is further multiplied by a distance coefficient. Assuming that the distance from the focal point of the X-ray tube 21 to each of the detector row j and channel i of the multi-row X-ray detector 24 corresponding to the projection data Dr is r0, and the distance from the focal point of the X-ray tube 21 to each pixel on the reconstruction area P corresponding to the projection data Dr is r1, the distance coefficient is given as $(r1/r2)^2$.

In the case of parallel beam image reconstruction, each pixel on the reconstruction area P may be multiplied by the cone beam reconstruction weight coefficient w (i, j) alone.

Figure 12:
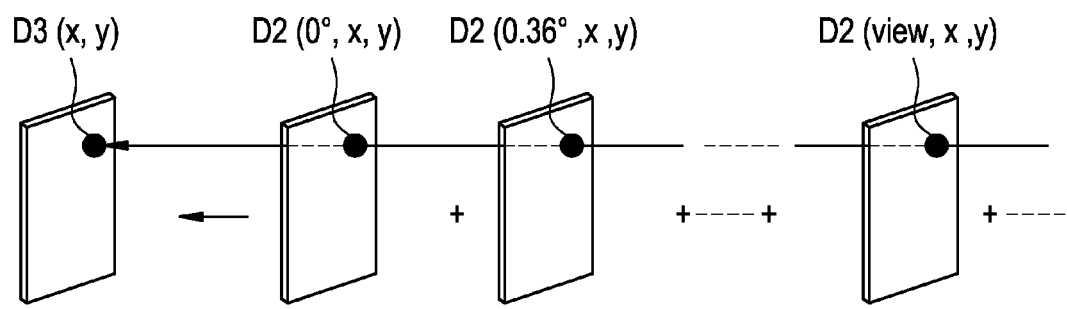
FIG. 12 is an explanatory diagram showing a state in which backprojection pixel data D2 are added together corresponding to pixels over all views to obtain backprojection data D3.

At Step S63, as shown in FIG. 12, the projection data D2 (view, x, y) is added to its corresponding backprojection data D3 (x, y) cleared in advance in association with each pixel.

Figure 13A:
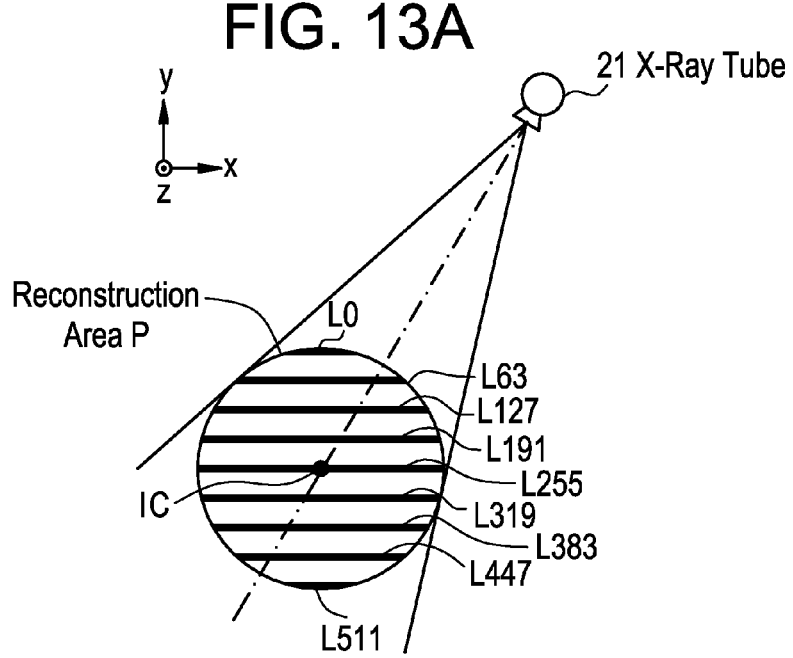
FIGS. 13a and 13b are conceptual diagrams illustrating a state in which lines on a circular reconstruction are projected in an X-ray penetration direction.
Figure 13B:
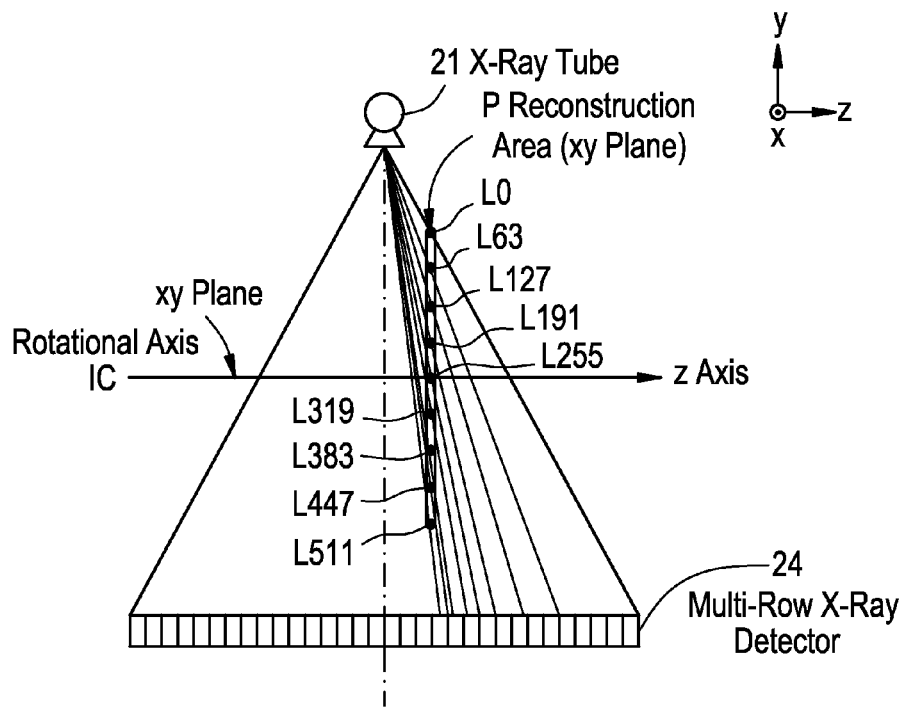

At Step S64, Steps S61 through S63 are repeated with respect to all the views (i.e., views corresponding to 360° or views corresponding to "180°+fan angles") necessary for image reconstruction of the tomographic image to obtain backprojection data D3 (x, y) as shown in FIG. 12. Incidentally, the reconstruction area P may be set as a circular area whose diameter is 512 pixels, without setting it as the square area of 512×512 pixels as shown in FIGS. 13(a) and 13(b).

Owing to the above image reconstruction method, each tomographic image on the xy plane orthogonal to the z direction corresponding to the travel direction of the photographing table 10 or the cradle 12 can consecutively be image-reconstructed. With the tomographic image continuous in the z direction as a three-dimensional image, an image brought to a two-dimensional image can be displayed on the monitor 6 by three-dimensional display methods used for an image three-dimensionally displayed in three-dimensional volume rendering representation, an MPR-displayed image, an MIP-displayed image, a reprojection-displayed image and the like.

When the three-dimensional image is set to the two-dimensional image by the above various methods, the sightline direction always exists and the image is processed in that direction so as to be formed as the two-dimensional image, followed by being displayed on the monitor 6. That is, the depth direction of the monitor 6 corresponds to the sightline direction.

Even when the spatial resolution of the image is degraded in the depth direction as viewed in the sightline, it is generally hard to be aware of it. Even in the case of, for example, a method in which an image is transparent and seen through in the depth direction as in the MIP display or the reprojection display, it is hard to be aware of degradation in the spatial resolution of the image as viewed in the depth direction. If a method in which no image is seen through in the depth direction as in the MPR display or the three-dimensional volume rendering display is taken, it is still hard to recognize degradation in spatial resolution of the image as viewed in the depth direction. In the present embodiment, this is taken as a point.

Figure 17:
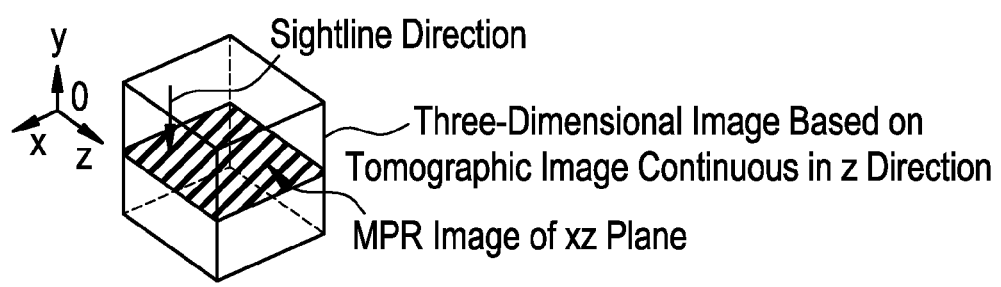
FIG. 17 is an explanatory diagram illustrating a sightline direction where an xz plane is MPR-displayed.

A noise reduction and an artifact reduction will be considered using the display-based characteristic of the three-dimensional image brought down to the two-dimensional image displayed on such a two-dimensional monitor 6. Generally, a tomographic image image-reconstructed on an xy plane is capable of making a reduction in noise and a reduction in artifact by applying a smoothing filter in the slice direction corresponding to the z direction. In FIG. 17 by way of example, a sightline direction at the time that an xz plane of a three-dimensional image based on a tomographic image continuous in a z direction is MPR-displayed results in a y direction. Since, in this case, no smoothing filter is applied in the x and z directions even though a one-dimensional smoothing filter is applied in the y direction, for example, degradation in spatial resolution by the one-dimensional smoothing filter as viewed in the y direction is not recognized from the sightline direction so long as the xz plane is seen.

Figure 18A:
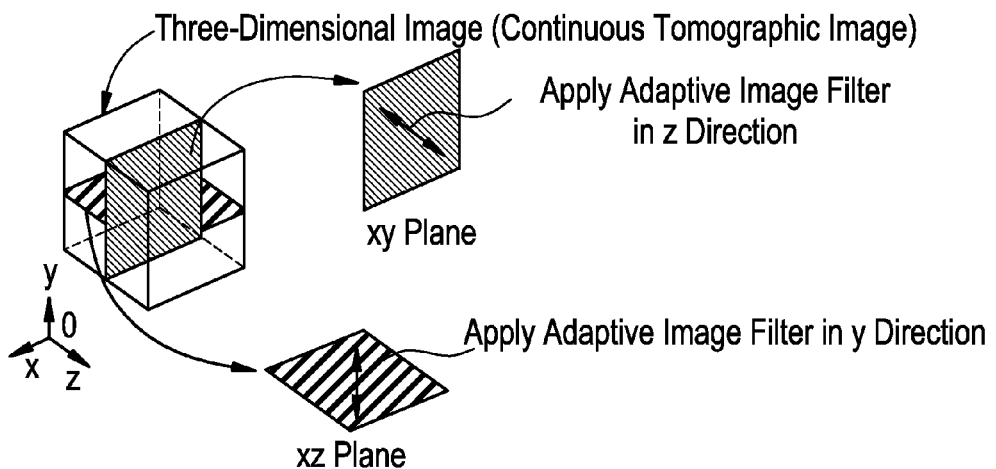
FIG. 18(a) is an explanatory diagram showing the direction in which an adaptive image filter is applied onto an MPR image of each of an xy plane and an xz plane.

Likewise, if an adaptive image filter or a smoothing filter is applied in a z direction, then no smoothing filter is applied in x and y directions when an xy plane is seen as shown in FIG. 18(a). Therefore, degradation in spatial resolution is not recognized from a sightline direction so long as the xy plane is seen.

Figure 18B:
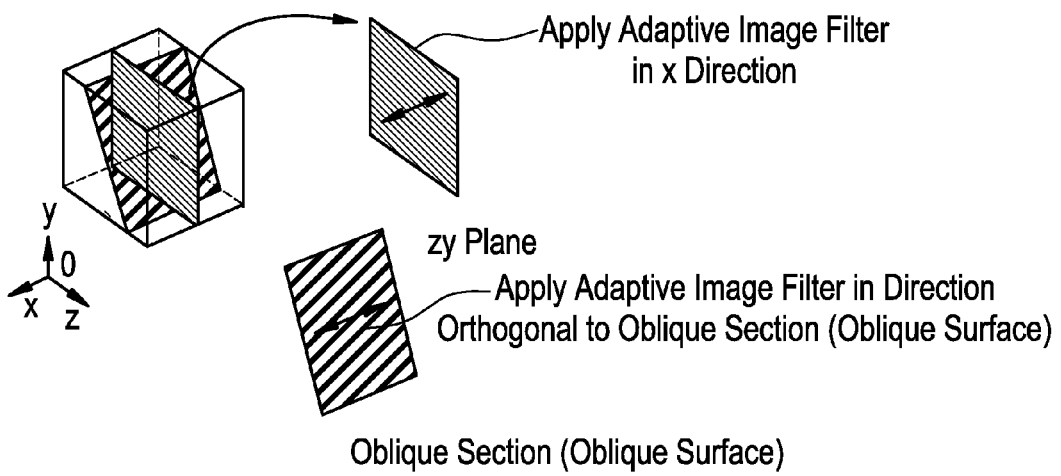
FIG. 18(b) is an explanatory diagram showing the direction in which an adaptive image filter is applied onto an MPR image on an oblique section.

If the adaptive image filter or smoothing filter is applied in the y direction, then no smoothing filter is applied in the x and z directions when an xz plane is seen. Therefore, degradation in spatial resolution is not recognized from a sightline direction so long as the xz plane is seen. Further, if the adaptive image filter or the smoothing filter is applied in the direction orthogonal to an oblique section, then no smoothing filter is applied in the direction parallel to the oblique section when the oblique section is seen as shown in FIG. 18(b). Therefore, degradation in spatial resolution is not recognized from a sightline direction so long as the oblique section is seen.

The reduction in noise and the reduction in artifact have recently been practicable without lowering the spatial resolution by using an adaptive filter without using a passive filter. Although the present embodiment has described the example in which the adaptive filter is used, similar advantageous effects are obtained even in the case of the passive filter.

Figure 16:
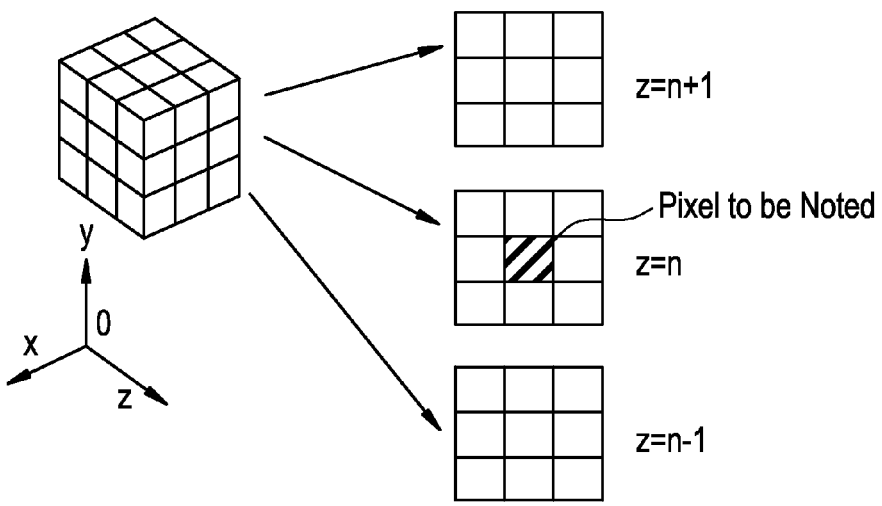
FIG. 16 is an explanatory diagram depicting a pixel to be noted and pixels adjacent thereto.

Consider where a passive three-dimensional image filter is taken for a centered pixel-of-interest and neighboring pixels of 26 pixels (3×3×3−1=26) lying in a range of 3×3×3 near to the pixel-of-interest when a local area of 3×3×3 corresponding to given part in a three-dimensional image is taken out as shown in FIG. 18, for example, a filter coefficient of 1/27 is added to all of a pixel-of-interest and neighboring pixels of 26 pixels (3×3×3−1=26) lying in a range of 3×3×3 located in the neighborhood thereof in an example 1 of a passive image filter shown in FIG. 16 by way of example. In doing so, a three-dimensional image filter is realized wherein the average value of 27 pixels in total equivalent to the 26 neighboring pixels and the pixel-of-interest is added to the pixel-of-interest. In a passive image filter illustrated as an example 2 of FIG. 16, the average value of 19 pixels equivalent to neighboring pixels and a pixel-of-interest is inserted into the pixel-of-interest. In a passive image filter illustrated as an example 3 of FIG. 16, the average value of 7 pixels equivalent to neighboring pixels and a pixel-of-interest is inserted into the pixel-of-interest.

In an active adaptive filter as shown in a first embodiment to be described later, a local image characteristic thereof is grasped and shape detection is performed, and noise can be reduced for every area according to the shape detection.

Generally, when the smoothing filter or the like is applied, a reduction in noise can be made but spatial resolution is degraded. In order to perform noise elimination and a reduction in noise without degrading the spatial resolution, it is ideal that the shape of an object in an image and its object area are determined and recognized or the boundary of the object, its profile, the object area and its edge are detected to enable the noise elimination while the profile and edge of the object are being stored, without impairing them.

The first, second and third embodiments described below respectively show an example illustrative of an adaptive noise elimination filter and an adaptive noise reduction filter, an example in which a noise reduction filter is applied in a sightline direction and a depth direction using it, and an example illustrative of a dynamic noise reduction filter at the time that a sightline direction changes.

First embodiment: it shows the example illustrative of the adaptive noise elimination filter and the adaptive noise reduction filter.

Second embodiment: it shows the example in which the noise reduction filter is applied in the depth direction when a three-dimensional image is displayed.

Third embodiment: it shows the example illustrative of the dynamic noise reduction filter at the time that the sightline direction changes where a three-dimensional image is displayed.

First Embodiment

In the first embodiment, an embodiment illustrative of an adaptive noise elimination filter and an adaptive noise reduction filter, which does not degrade spatial resolution, will be shown below. The present embodiment shows an image filter capable of simultaneously effecting improvements in S/N and noise and a reduction in artifact on a tomographic image of an X-ray CT apparatus principally without degrading the spatial resolution.

As its basic idea, recognition as to whether the respective pixels in the areas for the pixel-of-interest and the neighboring pixels thereof are structures or noise is made while adapting the edge detection to each pixel. It is thus possible to simultaneously efficiently perform contradictory processes of both storage of spatial resolution and smoothing, that a portion having a high-frequency component is retained and a noise portion is smoothed.

As a specific effect, the X-ray CT apparatus is effective in that when an X-ray tube current value is lowered to reduce X-ray exposure, a reduction in X-ray exposure is made to a subject. However, the S/N of an image is reduced and noise increases, thus causing degradation of diagnosability of a tomographic image of the X-ray CT apparatus. It is effective to realize an image filter which reduces noise even when the X-ray tube current is decreased to reduce X-ray dosage, for the purpose of improving such a point. If the spatial resolution of the structure in the tomographic image can further be retained or improved to provide enhancement or intensification, then the diagnosability of the tomographic image can be enhanced and made effective.

From such a background, there have been proposed various methods each of which retains or enhances the shape of a structure of a tomographic image and reduces only noise. Many of them include methods each of which observes continuity of its shape and enhances or reduces given specific frequency data on frequency space. Its shape detection algorithm is constant even with respect to any structure in the image. It is not practiced to grasp the characteristic of the image and make a further reduction in noise effectively and efficiently.

Based on the above background, the first embodiment shows the algorithm of the image filter that dynamically performs the shape detection so as to adapt to the characteristic of each image.

Figure 19:
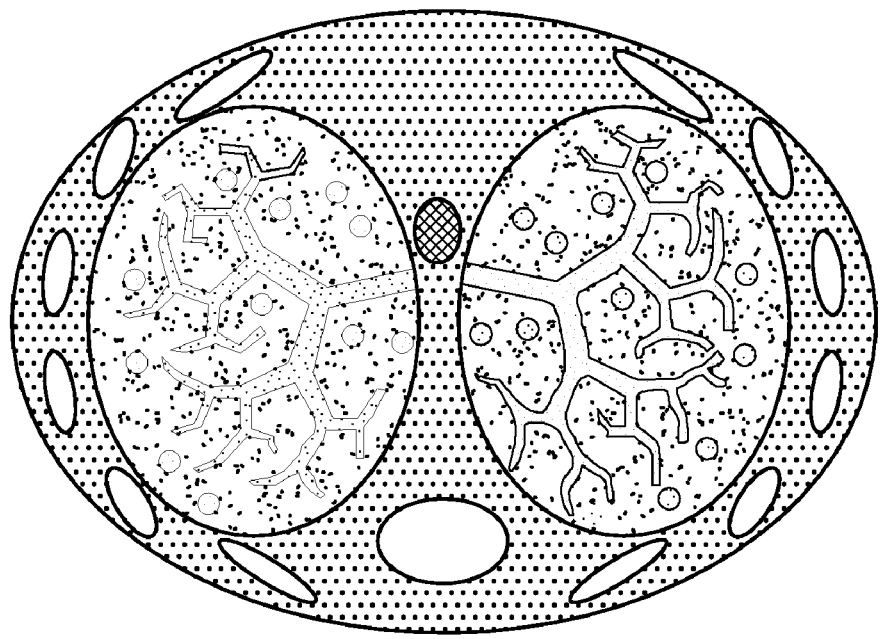
FIG. 19 is a typical diagram illustrating an original tomographic image.
Figure 20:
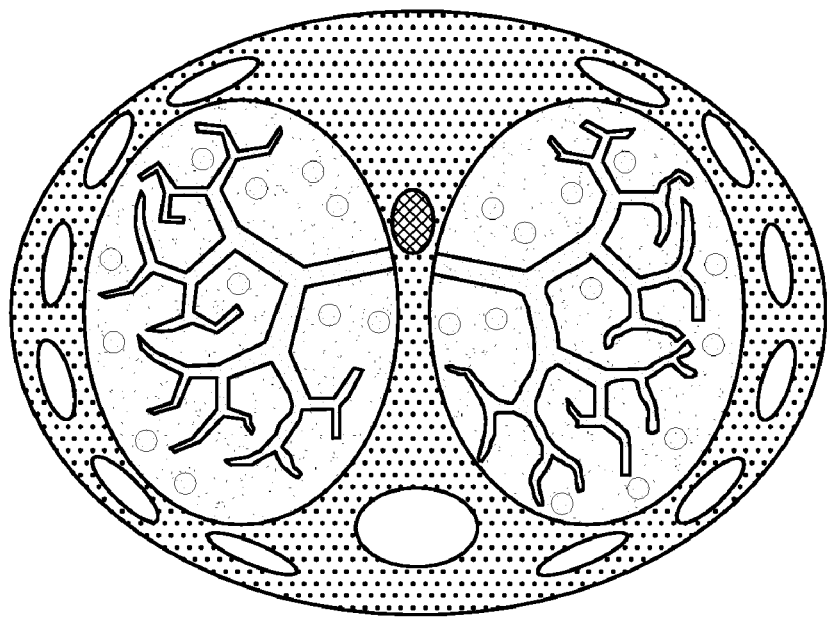
FIG. 20 is a typical diagram showing a tomographic image in which a noise reduction with no execution of edge storage is made.
Figure 21:
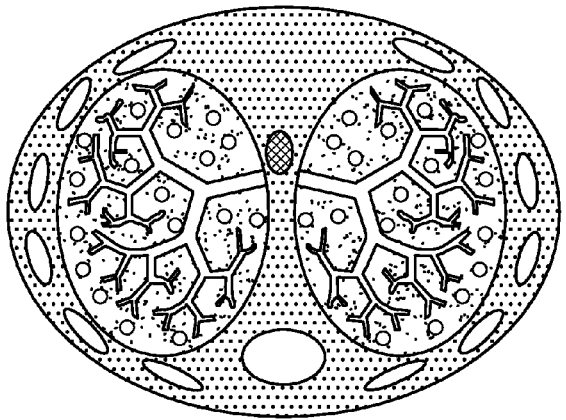
FIG. 21 is a typical diagram depicting a tomographic image in which a noise reduction with execution of edge storage is made.

An original tomographic image is first shown in FIG. 19. In the present example, the windpipe and blood vessels in the lung field are not clearly reflected and hard to recognize due to noise in an air area of the background on the image. An image in which noise is reduced from the image shown in FIG. 19, is next shown in FIG. 20. However, FIG. 20 shows an example in which smoothing free of execution of shape recognition for performing edge detection is made. In the example, fine structure parts like end portions such as the windpipe and the blood vessels are also blurred simultaneously with a reduction in noise, and spatial resolution is degraded, thereby often losing fine structure information. Further, an example shown in FIG. 21 shows the case of a noise reduction in which edge detection and edge enhancement are simultaneously performed. Smoothing with such edge enhancement makes it possible to sharpen even the fine structure parts and reduce noise simultaneously with it.

As examples described in the prior art, which simultaneously perform such edge enhancement, edge sharpening and noise smoothing, (1) the continuity of each shape and (2) the process of frequency space shown below will be considered.

(1) Consideration is given to the case in which the continuity of a shape is examined upon edge detection. When pixels adjacent to a given pixel to be noted have tendencies to show similar image characteristic quantities, they are recognized as being identical in shape and smoothing processing is made between the pixels. In a tomographic image obtained by the X-ray CT apparatus, for example, a CT value or a standard deviation thereof, etc. are considered as its image characteristic quantities. If the image characteristic quantities are found not to be structures each having a similar tendency, then sharpening processing is performed. In such a case, however, there are considered problems about how to define the tendencies to show the similar image characteristic quantities and how to define the tendencies to show the similar image characteristic quantities depending upon the type of shaped object. When objects having tendencies to show similar image characteristic quantities appear discontinuously where the continuity of each shape is seen, smoothing processing cannot be made between the discontinuous ones.

(2) Consider where an image is substituted with frequency space and a specific frequency component is enhanced or smoothed. In such a case, a technical difficulty is considered to exist in that any of frequency components should be recognized as being a change in shape or noise. Although, for example, more than the Nyquist frequency can also be considered to be noise components, unnatural artifacts appear on the image if frequency components more than the Nyquist are removed discontinuously. Artifacts like streak are not necessarily limited to the frequencies higher than the Nyquist. There is also a possibility that the frequency of a change in shape will also fall into the Nyquist or higher. Thus, it is difficult to define the Nyquist or more as noise all. The process on the frequency space makes it difficult to treat smoothing processing for edge storage with satisfactory accuracy.

Figure 22:
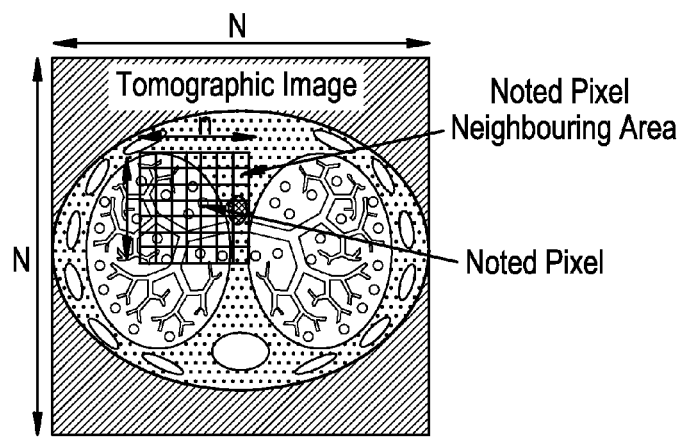
FIG. 22 is an explanatory diagram showing a pixel to be noted and an area adjacent to the pixel in a tomographic image.

In the first embodiment, the tomographic image of the X-ray CT apparatus is considered with a CT value corresponding to a pixel value as the base or reference. The features of the first embodiment will be descried in several tiers. A tomographic image, a noted image and a pixel-of-interest neighboring area at this time are given as shown in FIG. 22.

In the first embodiment, a criterion of judgment for edge shape recognition is dynamically changed according to the image characteristic quantities of the pixel-of-interest and its neighboring area. A standard deviation value of the CT value corresponding to the pixel value is considered as its criterion of judgment.

By dynamically changing the criterion for edge recognition, i.e., the criterion for sharpening and smoothing with the standard deviation value as the reference in accordance with the image characteristics of the pixel-of-interest and its neighboring area in this way, the smoothing processing is suppressed at a portion less reduced in noise and the adverse effect of smoothing is suppressed. This is, although the edge shape recognition will be described later, because it makes it easy to store the edge as the degree of smoothing becomes smaller even so. On the other hand, the smoothing processing is enhanced at a portion large in noise to obtain the effect of reducing noise. Thus, since the spatial resolution is degraded due to the adverse effect of noise or artifacts at the portion large in noise, a high-definition shape cannot be recognized originally and only a structure represented by a low-frequency component can be observed. Therefore, even though the smoothing processing is enhanced to some degree, the adverse effect of degradation in the edge corresponding to the structure can be less reduced.

Likewise even about the sharpening, a criterion of judgment for edge recognition, i.e., a criterion of judgment for sharpening and smoothing is dynamically changed with a standard deviation value as the reference in accordance with the image characteristics of a pixel-of-interest and its neighboring area. As a result, enhancement processing is performed where the edge is judged to exist. On the other hand, when the edge is judged not to exist, no enhancement processing is done. Thus, noise due to the adverse effect of the enhancement processing is not increased. Since the case in which the edge is judged to exist in this way is set so as not to be recognized as noise, this is not contradictory to the previously-mentioned noise smoothing processing.

As a specific edge shape recognition method, a standard deviation value of each pixel in a processing area or a function value with the standard deviation value as a variable is determined, a threshold value is determined from the standard deviation value, and smoothing processing is effected on the pixel lying in the threshold value as a similar structure. Thus, since the degree of smoothing is determined based on the standard deviation value, smoothing can be deenhanced at a portion low in noise and smoothing can be enhanced at a portion large in noise. If such processing is taken, it is then possible to detect pixels containing similar shaped objects discriminated based on a CT value corresponding to a pixel value and its standard deviation value even in the case of discontinuous pixels and effect smoothing processing thereon.

When, however, the standard deviation value lying in the processing area is simply determined, it is not possible to judge or determine whether noise increases and the standard deviation value is high or the standard deviation value is high because a structure is included in the processing area. If the standard deviation value becomes high because the structure is contained, and a high threshold value is set based on the high standard deviation value and as a result, smoothing processing is enhanced, then information about the structure is eventually lost. In order to prevent it, a local standard deviation value lying in the processing area is determined, and shape recognition is made as to whether the standard deviation value lying in the processing area corresponds to a standard deviation value based on the noise or a standard deviation value based on the structure.

The above local standard deviation value is determined and at the same time an overall standard deviation value in the processing area is also determined. When the local standard deviation value is sufficiently smaller than the overall standard deviation value, it is judged that the structure exists in the processing area. Pixels different in structure are discriminated with the threshold value determined in the above as the reference, and enhancement processing is effected on the pixels.

Figure 27:
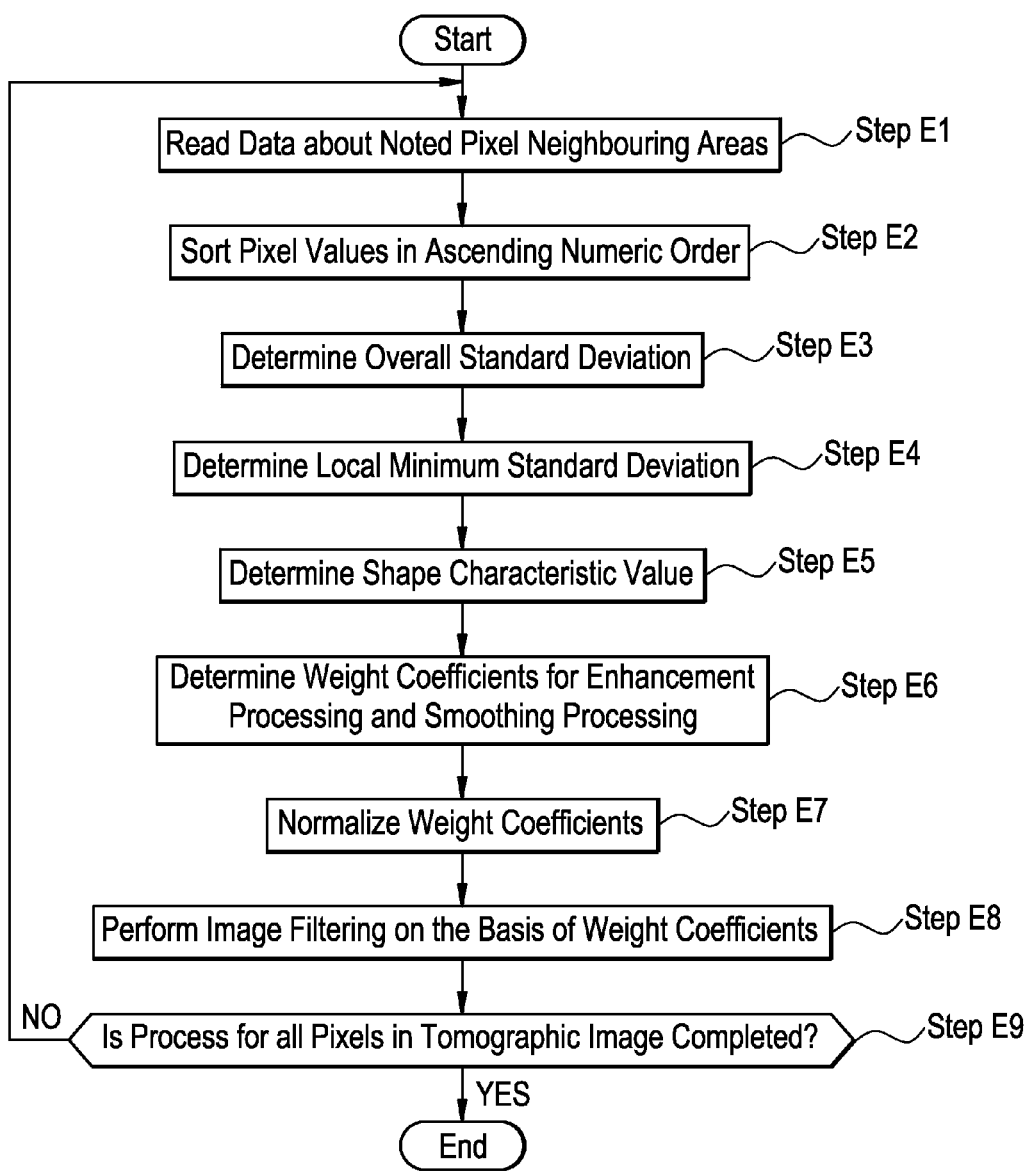
FIG. 27 is a flow chart depicting the operation of an adaptive noise reduction filter in which spatial resolution is held or enhanced.

FIG. 27 shows a simple flow chart showing the operation of an adaptive noise reduction filter according to the first embodiment in which spatial resolution is maintained or enhanced. In accordance with the flow chart, processing is executed in the following order.

At Step E1, data about each pixel-of-interest neighboring area is read.

At Step E2, pixel values are sorted in ascending numeric order.

At Step E3, an overall standard deviation corresponding to an overall standard deviation value in each processing area is determined.

Figure 23:
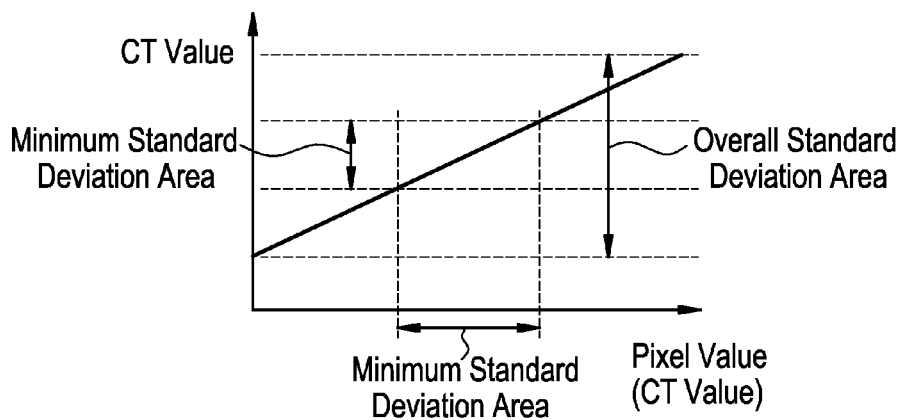
FIG. 23 is an explanatory diagram illustrating a uniform CT value distribution in a pixel-of-interest nearby area where no specific structure exists.

At Step E4, a minimum standard deviation value corresponding to a local standard deviation value is determined. A minimum standard deviation area corresponding to a data size for the local standard deviation value is adjustable as one parameter. When no specific structure exists within a neighboring pixel and its neighboring pixel area at this time, a distribution of sorted data in the processing area is considered to take such a monotonously increased shape as not to have a specific flat portion as shown in FIG. 23. Alternatively, the distribution is considered to become a graph flat as a whole. However, this is considered as a case small in tilt of FIG. 23. If, at this time, the minimum standard deviation area corresponding to the data size for the local standard deviation value is set to about ⅓ of a data size of the processing area, then the difference between the overall standard deviation value and the minimum standard deviation value is considered to be a difference of three times or so as shown in FIG. 23.

Figure 24:
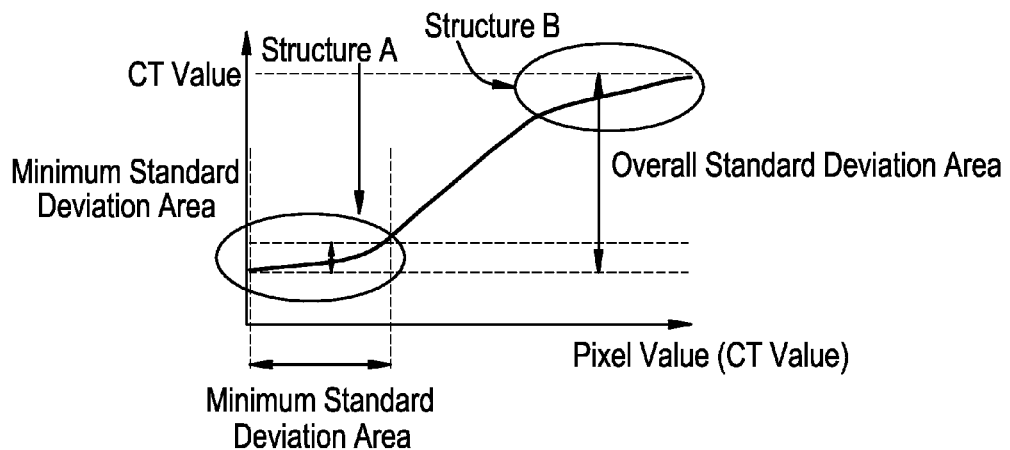
FIG. 24 is an explanatory diagram showing an example 1 of a CT value distribution in a non-uniform pixel-of-interest nearby area where structures A and B exist.
Figure 25:
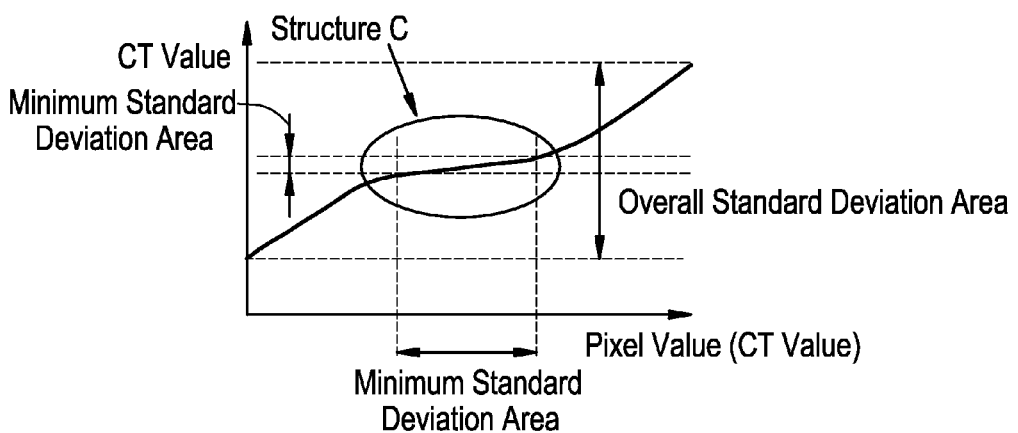
FIG. 25 is an explanatory diagram illustrating an example 2 of a CT value distribution in a non-uniform pixel-of-interest nearby area where a structure C exists.
Figure 26:
FIG. 26 is an explanatory diagram showing an area located in the neighborhood of a pixel to be noted.

At Step E5, when a specific structure exists in the processing area in contrast, a data distribution lying in the processing area sorted as shown in FIG. 24 or 25 is considered to be divided into a specific flat portion and a tilted portion as a trend. When, however, consideration is made as to whether structures exist in portions at which such CT values as viewed through these graphs are transitioned, there is considered a possibility that the structures will exist even in the transition portions in practice. However, when limited to within the local processing area, the structure is considered to be still observed as the flat portion of the data distribution as shown in FIG. 24 or 25 where the structure exists. If such a local processing area as shown in FIG. 26, for example, is taken into consideration, then an air portion can also be separated into two structures of windpipe/blood vessels in the lung field and air for its background where the air portion is considered as the structure in the present example. The windpipe/blood vessels and the air portion are considered to be separable into two flat histogram distributions of CT values respectively. When an image at a tilted portion of the histogram distribution is observed at the tilted portion, its noise cannot be observed in detail because the histogram distribution of CT values is not flat. Since structures typified by flat data distributions of CT values can easily be observed in noise in reverse, these flat portions are focused or noted and intended for processing.

Thus, the flat local standard deviation value is defined as the minimum standard deviation value. Thus, when each structure exists in the processing area and does not exist therein, the local minimum standard deviation value greatly differs. In other words, the structures lying in the processing area can be distinguished from each other by the minimum standard deviation value.

However, the overall standard deviation value and the minimum standard deviation value are compared with each other to more accurately confirm the existence of each structure in the processing area. If the data size for the local standard deviation value is set to about ⅓ of the data size of the processing area as described above and where the structures exist in the processing area, the overall standard deviation value and the minimum standard deviation value greatly differ as shown in FIGS. 24 and 25. Comparing the overall standard deviation value and the minimum standard deviation value in this way makes it possible to judge whether the corresponding structure exists in the processing area.

An index indicative of the degree as to whether the structure exists in the processing area as described above is determined as a shape characteristic value. The shape characteristic value is calculated from the ratio between the overall standard deviation value and the minimum standard deviation value as described above.

At Step E6, the minimum threshold value and the maximum threshold value are determined from the minimum standard deviation value determined as described above. By multiplying the minimum standard deviation values by adjustable coefficients, for example, their threshold values are determined. At this time, the number of the threshold values may be one or three or more without being fixed to the two.

It is judged whether enhancement processing is effected on each pixel in the processing area using the shape characteristic value determined in the above-described manner or smoothing processing is effected thereon. When the enhancement processing is performed, the maximum threshold value is further compared with it. If it is larger than that, then the pixels are recognized as being different shaped objects and weight coefficients for enhancement (sharpening) processing are determined.

Weight coefficients for image smoothing in the processing area are determined using the minimum threshold value and maximum threshold value determined in the above-described manner. For example, the weight coefficient relative to each pixel lying within the minimum threshold value is set to 1, the weight coefficient relative to each pixel lying within the maximum threshold value is set to 0.5, and the weight coefficient exceeding the maximum threshold value is set to 0.0. Alternatively, there is also considered a method for preparing a computational equation and determining weight coefficients so as to gently change according to the threshold values. Thus, the pixels lying within a given constant CT value are judged to be the same structures depending upon the minimum standard deviation value, and smoothing is performed between the pixels of the structures identical to each other. When it is determined that the difference of some degree or more exists by comparison with the maximum threshold value and the structures that differ depending on the shape characteristic value exist, a weight coefficient for enhancement processing which performs sharpening, is determined.

At Step E7, the respective weight coefficient values are normalized so as to be 1.0 as an overall sum.

At Step E8, smoothing is performed between the pixels considered to be the same structures in this way to enable an improvement in noise. Further, enhancement processing is performed between the pixels of the different structures to make it possible to more sharpen the boundary between the structures and perform edge enhancement. Since the smoothing and sharpening at this time are dynamic depending upon the image characteristic quantity of the processing area, an efficient and effective process can be carried out.

At Step E9, it is determined whether a process for the area in the tomographic image is completed. If the answer is found to be YES, then the process is ended. If the answer is found to be NO, then the process is returned to Step E1. As effects obtained in the first embodiment, it is possible to retain and improve the spatial resolution of each structure in the tomographic image of the X-ray CT apparatus and reduce noise. As a result, even though X-ray exposure dosage is reduced, a noise's tomographic image similar to the conventional one can be obtained. Consequentially, X-ray exposure for the subject can be reduced.

Since the smoothing for the noise reduction and the enhancement processing for the enhancement of resolution can be dynamically changed, the degree of smoothing is less reduced and at the same time the resolution of the structure is enhanced in the local processing area unnecessary to perform the noise reduction. At such a portion large in noise as to contain the streak and artifacts in reverse, the degree of smoothing can be enhanced and the degree of a reduction in noise can be increased. Thus, since the detailed structure is originally collapsed at the portion large in noise, the adverse effect on the spatial resolution is not large even if the degree of smoothing is enhanced to some extent. As another effect, the streak can also be reduced with being recognized as noise.

Although the shape recognition has principally been performed using the two-dimensional image as one sheet of tomographic image in the present embodiment, the shape recognition can also be carried out using a three-dimensional image as plural sheets of tomographic images. When the shape recognition is performed using the three-dimensional image in this way, it is considered that the shape recognition can be performed more accurately in terms of large quantities of information.

Further, the idea of the first embodiment can also be developed even to general moving pictures. For instance, a plurality of sheets of general two-dimensional images are observed or monitored with respect to the time base and their shapes are recognized. Portions motionless within the images can be removed in noise while the resolutions of their shapes are being improved, whereas moving portions are regarded to be large in noise if taken as plural images on the time base, so that smoothing processing is enhanced. Since, however, the moving portions are originally low in resolution recognizable by the human eyes, setting a smooth image even through the enhancement of the smoothing processing is felt or recognized as being low in noise. Simultaneously, a portion less reduced in motion is sharpened and smoothed and is easy to realize an improvement in image quality. Thus, the first embodiment can dynamically effect shape recognition, edge enhancement and smoothing even on general moving pictures and can perform further effective and efficient image processing.

As the image processing for the conventional edge enhancement and noise smoothing, there is considered an observation of continuity of a structure constituted of its edge or a frequency-based operation. However, the degree of its retention or the enhancement of smoothing does not vary dynamically. Since the enhancement of its sharpening and smoothing is dynamically changed in the first embodiment, the sharpening of the structure and the noise reduction can effectively be performed depending upon the local processing areas. As a result, when it is considered that the conventional edge enhancement and noise smoothing could be set to the same degree as conventional, noise can effectively be reduced at the portion large in noise than conventional. Since the portion including the artifacts such as streak is recognized as large in noise, novelty exists even in that there is an effect that the streak is reduced.

Second Embodiment

The first embodiment has shown the embodiment illustrative of the adaptive noise elimination filter and the adaptive noise reduction filter that do not degrade the spatial resolution. A second embodiment will show an example in which an adaptive noise reduction filter that does not degrade its spatial resolution is applied in a depth direction and a sightline direction at the display of a three-dimensional image.

Figure 28:
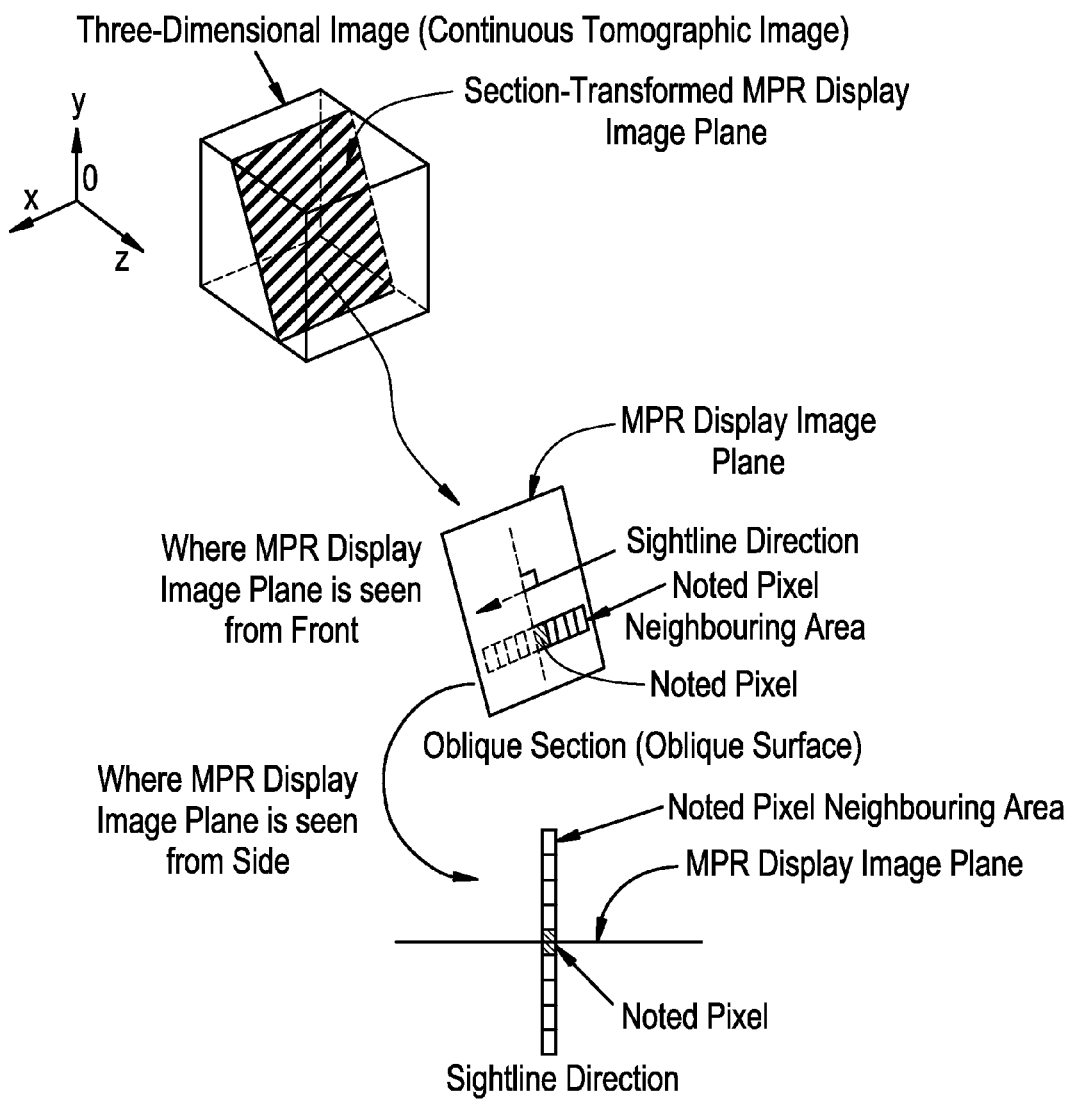
FIG. 28 is an explanatory diagram showing pixel-of-interest nearby areas expanded in a sightline direction and a one-dimensional direction of an MPR display image plane.

Such neighboring pixels as shown in FIG. 16 have been taken into consideration in the first embodiment. Since, however, the neighboring pixel areas are expanded in the x, y and z directions, the effect is not limited to the sightline direction alone but uniformly brought about in the x, y and z directions. For instance, an MPR display image plane in which a three-dimensional image of a continuous tomographic image is section-transformed is shown in FIG. 28. When the MPR display image plane is seen from the front, the sightline direction results in the direction orthogonal to the MPR display image plane. In this case, areas adjacent to a pixel-of-interest are taken parallel to the sightline direction.

Figure 30A:
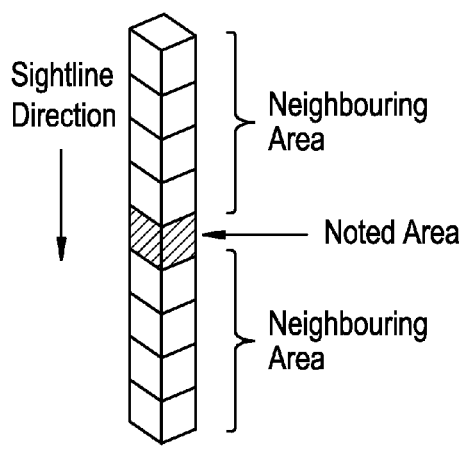
FIG. 30(a) is an explanatory diagram showing pixel-of-interest nearby areas of a one-dimensional image filter.

The pixel-of-interest and the pixel-of-interest neighboring areas are taken perpendicular to the MPR display image plane as shown in FIG. 28, for example. An example illustrative of pixel-of-interest neighboring areas of a one-dimensional filter at the time that one pixel-of-interest and eight neighboring pixels are provided is shown in FIG. 30(a). An adaptive filter can be realized which holds or enhances such spatial resolution as described in the first embodiment and reduces noise in the pixel-of-interest neighboring areas. Convolving the one-dimensional filter onto all pixels of an MPR display image enables a noise reduction with the retention or enhancement of the spatial resolution.

Since the smoothing of the pixel is performed only in a sightline direction in this case, the pixel blurs only in a depth direction corresponding to the direction parallel to the sightline, and the pixel does not blur in the direction unparallel to the sightline. That is, the blurring of the pixel is not recognized visually. Incidentally, even when the neighboring areas with respect to the pixel-of-interest take the other number of pixels without using the eight pixels, similar effects can be expected.

Figure 31A:
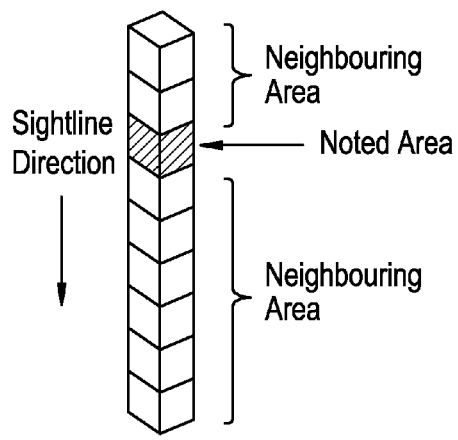
FIG. 31(a) is an explanatory diagram showing pixel-of-interest nearby areas of an asymmetric one-dimensional image filter.

The pixel-of-interest neighboring areas do not necessarily require the symmetry thereof set backward and forward as viewed in the sightline direction with the pixel-of-interest as the center. Even when they are set asymmetric, similar effects can be expected. An example illustrative of pixel-of-interest neighboring areas of an asymmetric one-dimensional filter is shown in FIG. 31(a).

Figure 29:
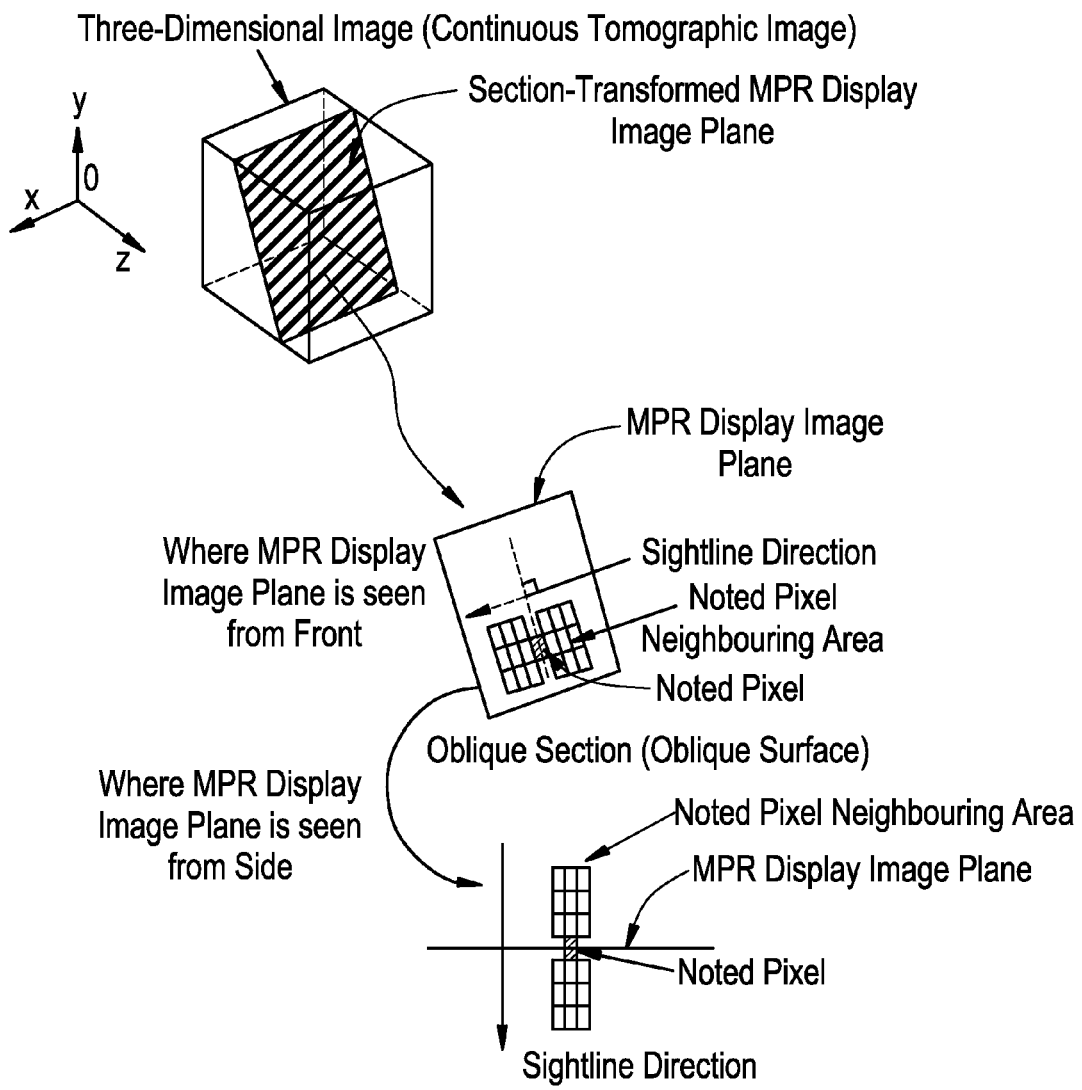
FIG. 29 is an explanatory diagram illustrating pixel-of-interest nearby areas expanded in a sightline direction and a two-dimensional direction of an MPR display image plane.

While the example of the one-dimensional filter is shown in FIG. 28, an example illustrative of a two-dimensional image filter is next shown in FIG. 29. FIG. 29 shows an MPR display image plane in which a three-dimensional image of a continuous tomographic image is section-transformed in a manner similar to FIG. 28. When the MPR display image plane is seen from the front, a sightline direction results in the direction orthogonal to the MPR display image plane. In this case, areas adjacent to a pixel-of-interest are taken parallel to the sightline direction.

Figure 30B:
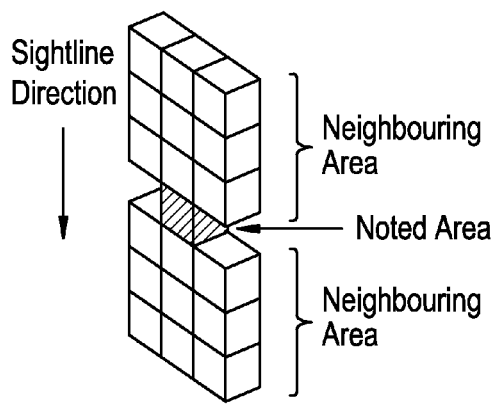
FIG. 30(b) is an explanatory diagram showing pixel-of-interest nearby areas of a two-dimensional image filter.

A pixel-of-interest and two-dimensional neighboring areas are taken perpendicular to the MPR display image plane as shown in FIG. 29, for example. An example illustrative of pixel-of-interest neighboring areas of a two-dimensional image filter at the time that one pixel-of-interest and two-dimensionally expanded eighteen (=3×3×2) neighboring pixels are provided is shown in FIG. 30(b).

Incidentally, since the pixels lying in the surface of the MPR display image are displayed in this case, the pixels lying in a layer following the surface or a layer prior to the surface are not displayed. Therefore, even when the pixels lying in the layer following or prior to the surface or a layer further following or prior to the following layer are used for a reduction in noise, spatial resolution of each pixel lying in the surface of the MPR display image is not lost. Therefore, the two-dimensionally expanded pixel-of-interest neighboring areas effectively act on the layer following the surface or its inner layer, or the layer prior to the surface or the layer lying ahead thereof.

An adaptive filter can be realized which maintains or enhances such spatial resolution as described in the first embodiment and reduces noise in the pixel-of-interest neighboring areas. Convolving the two-dimensional image filter onto all pixels of the MPR display image enables a noise reduction with the retention or enhancement of the spatial resolution.

In this case, pixel smoothing is effected only on the pixel-of-interest neighboring areas two-dimensionally expanded in the sightline direction and in the layer following the surface of the MPR display image or its inner layer, or the layer prior to the surface or the layer lying ahead thereof. Therefore, the pixels blur only in the depth direction corresponding to the direction parallel to the sight line and do not blur in the direction unparallel to the sightline. That is, the blurring of the pixel is not recognized visually.

Figure 31B:
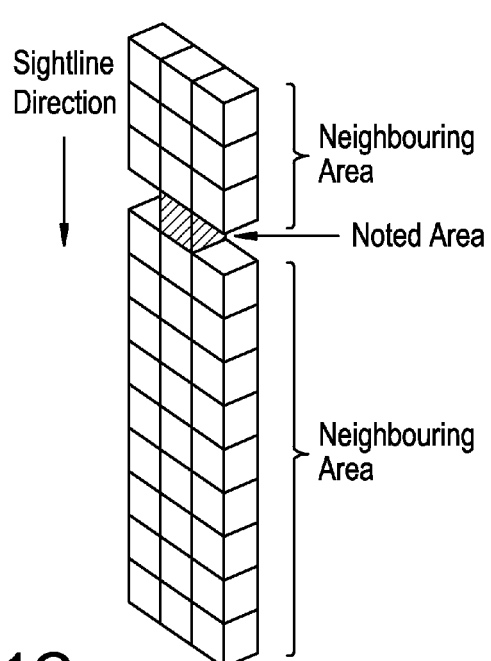
FIG. 31(b) is an explanatory diagram showing pixel-of-interest nearby areas of an asymmetric two-dimensional image filter.

Incidentally, even when the neighboring areas with respect to the pixel-of-interest take the other number of pixels without using the eighteen pixels necessarily, similar effects can be expected. The pixel-of-interest neighboring areas do not necessarily require the symmetry thereof set backward and forward as viewed in the sightline direction with the pixel-of-interest as the center. Even when they are set asymmetric, similar effects can be expected. An example illustrative of pixel-of-interest neighboring areas of an asymmetric two-dimensional filter is shown in FIG. 31(b).

Figure 30C:
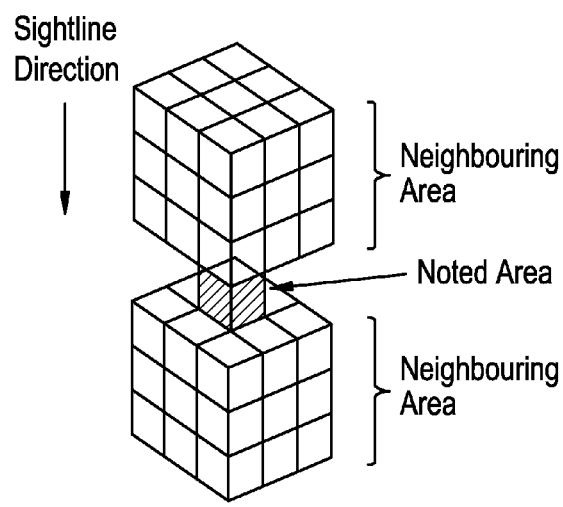
FIG. 30(c) is an explanatory diagram showing pixel-of-interests nearby areas of a three-dimensional image filter.
Figure 32:
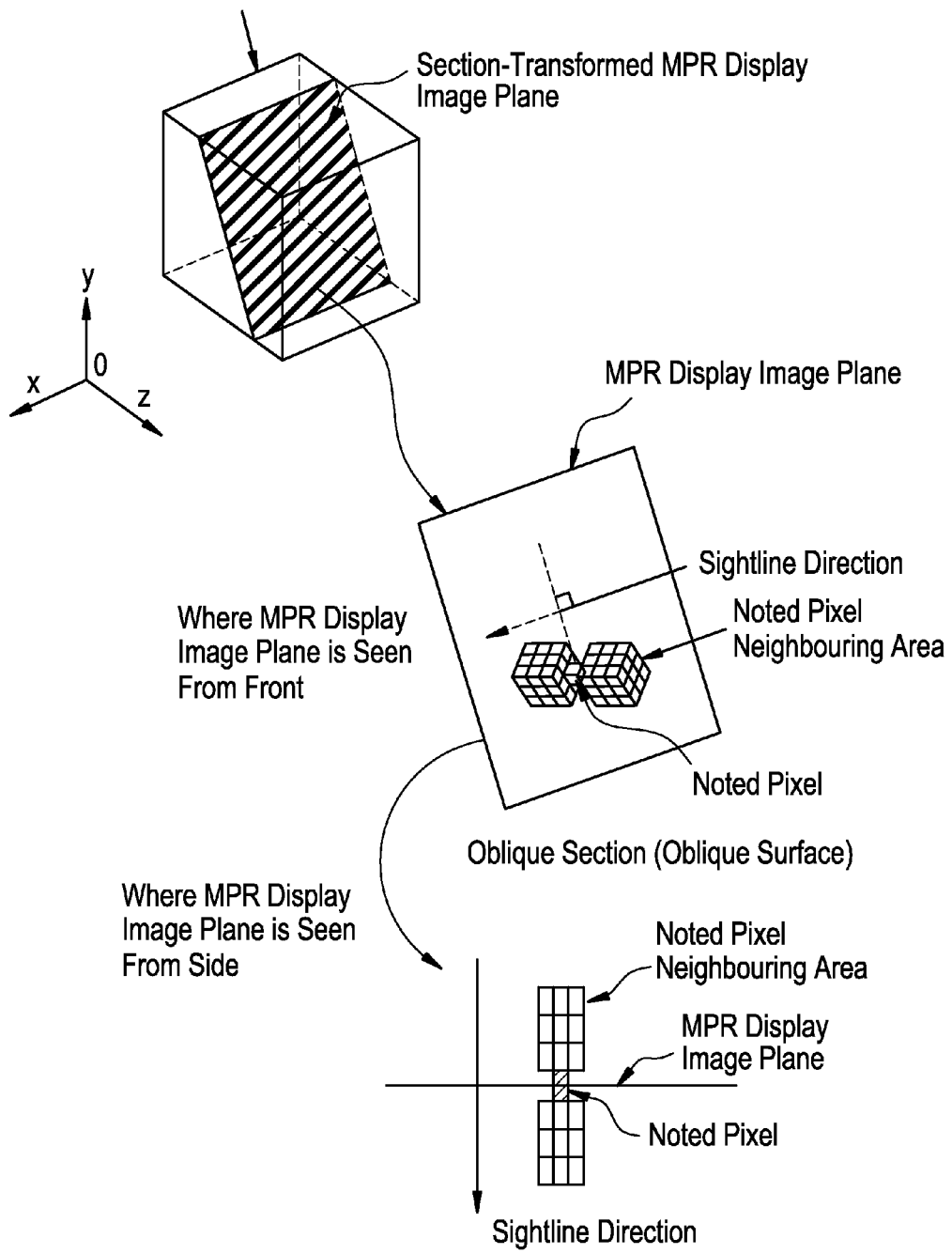
FIG. 32 is an explanatory diagram illustrating pixel-of-interest nearby areas expanded in a sightline direction and a three-dimensional direction of an MPR display image plane.

While the example of the one-dimensional filter is shown in FIG. 28 and the example of the two-dimensional image filter is shown in FIG. 29, an example illustrative of a three-dimensional image filter is next shown in FIG. 32. FIG. 32 shows an MPR display image plane in which a three-dimensional image of a continuous tomographic image is section-transformed in a manner similar to FIG. 29. When the MPR display image plane is seen from the front, a sightline direction results in the direction orthogonal to the MPR display image plane. In this case, areas adjacent to a pixel-of-interest are taken parallel to the sightline direction. A pixel-of-interest and three-dimensional neighboring areas are taken perpendicular to the MPR display image plane as shown in FIG. 32, for example. An example illustrative of pixel-of-interest neighboring areas of a three-dimensional image filter at the time that one pixel-of-interest and three-dimensionally expanded fifty-four (=3×3×3×2) neighboring pixels are provided is shown in FIG. 30(c).

Incidentally, since the pixels lying in the surface of the MPR display image are displayed in this case, the pixels lying in a layer following the surface or a layer prior to the surface are not displayed. Therefore, even when the pixels lying in the layer following or prior to the surface or a layer further following or prior to the following layer are used for a reduction in noise, spatial resolution of each pixel lying in the surface of the MPR display image is not lost. Therefore, the three-dimensionally expanded pixel-of-interest neighboring areas effectively act on the layer following the surface or its inner layer, or the layer prior to the surface or the layer lying ahead thereof.

An adaptive filter can be realized which maintains or enhances such spatial resolution as described in the first embodiment and reduces noise in the pixel-of-interest neighboring areas. Convolving the three-dimensional image filter onto all pixels of the MPR display image enables a noise reduction with the retention or enhancement of the spatial resolution.

In this case, pixel smoothing is effected only on the pixel-of-interest neighboring areas three-dimensionally expanded in the sightline direction and in the layer following the surface of the MPR display image or its inner layer, or the layer prior to the surface or the layer lying ahead thereof. Therefore, the pixels blur only in the depth direction corresponding to the direction parallel to the sightline and do not blur in the direction unparallel to the sightline. That is, the blurring of the pixel is not recognized visually.

Figure 31C:
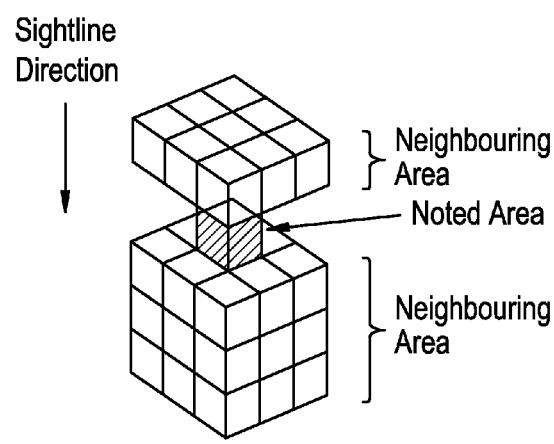
FIG. 31(c) is an explanatory diagram showing pixel-of-interest nearby areas of an asymmetric three-dimensional image filter.

Incidentally, even when the neighboring areas with respect to the pixel-of-interest take the other number of pixels without using the fifty-four (=3×3×3×2) pixels necessarily, similar effects can be expected. The pixel-of-interest neighboring areas do not necessarily require the symmetry thereof set backward and forward as viewed in the sightline direction with the pixel-of-interest as the center. Even when they are set asymmetric, similar effects can be expected. An example illustrative of pixel-of-interest neighboring areas of an asymmetric three-dimensional filter is shown in FIG. 31(c).

As described above, the second embodiment has shown the example in which the adaptive noise reduction filter that takes the MPR display image for example and does not degraded the spatial resolution, is applied in the depth direction and the sightline direction at the display of the three-dimensional image. Incidentally, even when a volume rendering image, an MIP display image and a reprojection image other than the MPR display image are taken as the three-dimensional image, similar effects can be expected.

Third Embodiment

A third embodiment shows an example of a dynamic noise reduction filter where a sightline direction at the display of a three-dimensional image is changed. Although the second embodiment has shown the example in which the noise reduction filter is applied in the depth direction at the display of the three-dimensional image, it shows that the present embodiment is effective even where the noise reduction filter is dynamically changed.

Generally, a three-dimensional image shown in three-dimensional representation may preferably be seen as if a subject were rotated by making a change in the sightline direction rather than its display in one sightline direction because it makes it easy to understand the expanse of three-dimensional space. Upon execution of three-dimensional volume rendering for displaying a lung field and contrasted blood vessels as shown in FIG. 33, for example, varying the sightline direction is effective where the expanse of each hidden portion is not found or recognized.

Figure 34:
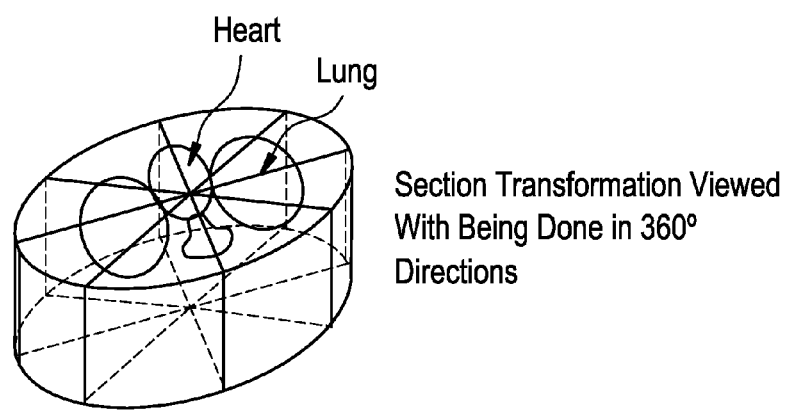
FIG. 34 is an explanatory diagram showing changes in section-transformation viewfield direction of an MPR display.

As shown in FIG. 34 in like manner, the expanses of a lung field and contrasted blood vessels in the respective directions are recognized by turning, 360°, each image represented in section with a z axis as the center even in the case of an MPR display image. Even in the case, varying a sightline direction is effective.

Figure 33:
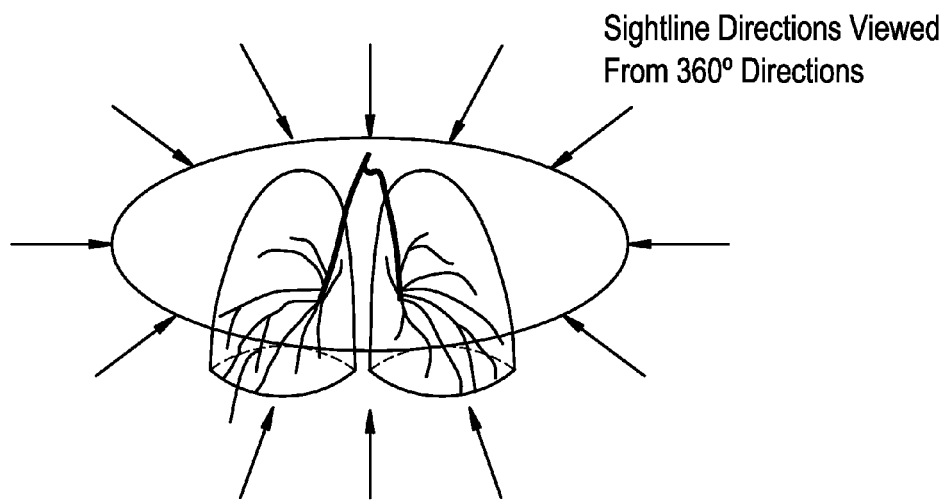
FIG. 33 is an explanatory diagram showing changes in sightline direction of a three-dimensional display image.

Even in the case of FIGS. 33 and 34, the following methods are considered as the direction in which the sightline direction is changed.

(1) Auto: The direction is automatically changed from 0° to 360°.

(2) Manual: The interested sightline-direction neighborhood is manually changed to check or look at the degree of a change in image.

Figure 35:
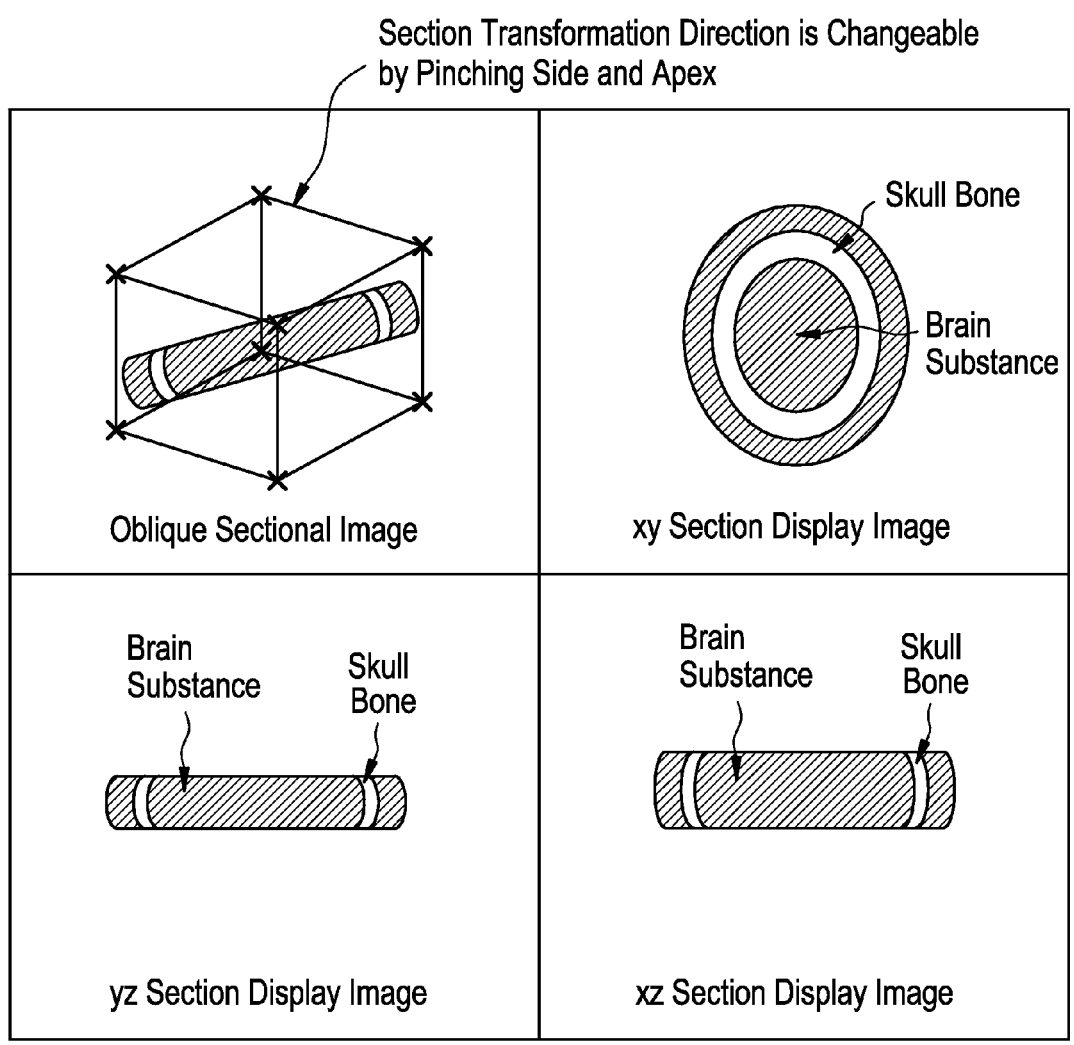
FIG. 35 is an explanatory diagram showing an example illustrative of three-dimensional section display screens.

A user interface in which the sightline direction is changed in the manual case is shown in FIG. 35. A cubic frame overlap-displayed on an oblique sectional image on the upper left screen of FIG. 35 is nipped or pinched with a mouse and dragged. Then, the cubic is rotated on a three-dimensional space basis to make it possible to vary the sightline direction of the oblique section display image within the three-dimensional space. A noise reduction filter is applied in the inner direction of a two-dimensional image displayed each time the sightline direction changes, thereby making it possible to always display an oblique section which is reduced in noise, decreased in artifact and undegraded in spatial resolution.

In the above X-ray CT apparatus 100, according to the X-ray CT apparatus or the X-ray CT imaging method, when tomographic images at a conventional scan (axial scan) or a cine scan, a cine scan, a helical scan, a variable pitch helical scan or a helical shuttle scan of the X-ray CT apparatus having a two-dimensional X-ray area detector of a matrix structure typified by a multi-row X-ray detector or a flat panel X-ray detector are arranged in a z direction and three-dimensionally displayed as a continuous tomographic image, a three-dimensional display image can be displayed in which S/N is improved from any sightline direction and artifacts are reduced, and spatial resolution is not degraded. That is, an X-ray CT apparatus can be provided which is capable of realizing an improvement in the image quality of the three-dimensional display image.

Although the MPR display has been described as the center in the present embodiment, similar effects can be brought about even in the case of an image shown in volume rendering three-dimensional image representation, an MIP-displayed image and a reprojection-displayed image.

The image reconstructing method according to the present embodiment may be a three-dimensional image reconstructing method based on a conventional known Feldkamp method. Further, another three-dimensional image reconstructing method may be adopted. Alternatively, two-dimensional image reconstruction may be used.

Although the present embodiment has been described based on the conventional scan (axial scan), similar effects can be brought about even in the case of a cine scan, a helical scan, a variable pitch helical scan and a helical shuttle scan.

Although the present embodiment has been described where the scan gantry 20 is not tilted, similar effects can be brought about even in the case of a so-called tilt scan at which the scan gantry 20 is tiled.

Although the present embodiment has been described where synchronization with the biological signal is made, similar effects can be brought about even when synchronization with a biological signal, particularly, a cardiac signal is taken.

Although the present embodiment has described the X-ray CT apparatus having the two-dimensional X-ray area detector having the matrix structure, which is typified by the multi-row X-ray detector or the flat panel X-ray detector, similar effects can be brought about even in the case of an X-ray CT apparatus having a one-row X-ray detector.

In the present embodiment, the row-direction (z-direction) filters different in coefficient for every row are convolved to adjust variations in image quality, thereby realizing uniform slice thickness, artifact and noise for each row. Although various z-direction filter coefficients are considered therefor, any can bring about similar effects.

Although the present embodiment has been explained with the medical X-ray CT apparatus as the base, it is available for an X-ray CT-PTE apparatus, an X-ray CT-SPEC apparatus and the like combined with an industrial X-ray CT apparatus or other apparatus.

The invention claimed is:

1. An X-ray CT apparatus comprising:
    an X-ray data acquisition device configured to acquire X-ray projection data transmitted through a subject positioned between an X-ray generator and a two-dimensional X-ray area detector configured to detect X-rays and positioned opposite the X-ray generator, the X-ray generator and the two-dimensional X-ray area detector rotatable about a center of rotation corresponding to a position of the subject;
    an image reconstructing device configured to reconstruct the projection data acquired from the X-ray data acquisition device to generate a tomographic image;
    an image display device configured to display a two-dimensional image extracted from a three-dimensional tomographic image continuous in a z-direction corresponding to a direction of travel of a cradle supporting the subject;
    an imaging condition setting device configured to set imaging conditions used for acquiring the projection data and displaying the tomographic image; and
    an image filter processing device configured to:
        define a pixel of interest in the two-dimensional image and at least one pixel neighboring the pixel of interest in the three-dimensional tomographic image, the at least one neighboring pixel positioned with respect to the pixel of interest in a direction orthogonal to the two-dimensional image; and
        perform an image filter processing for the pixel of interest in the two-dimensional image, wherein said image filter process varies depending on an image characteristic quantity of the at least one neighboring pixel.

2. The X-ray CT apparatus according to claim 1, wherein the image filter processing varies image filter coefficients for image filter processing.

3. The X-ray CT apparatus according to claim 1, wherein said image filter processing device performs the image filter processing using an adaptive image filter based on image characteristic quantities of the pixel of interest subjected to the image filter processing and the neighboring pixel adjacent to the pixel of interest.

4. The X-ray CT apparatus according to claim 3, wherein the image characteristic quantities contain CT values for the pixel of interest and the adjacent neighboring pixel.

5. The X-ray CT apparatus according to claim 4, wherein the image characteristic quantities contain standard deviations of the CT values for the pixel of interest and the adjacent neighboring pixel.

6. The X-ray CT apparatus according to claim 1, wherein the two-dimensional image comprises at least one of an MPR (Multi Plane Reformat) image and an MIP (Maximum Intensity Projection) image.

7. The X-ray CT apparatus according to claim 1, wherein the image filter processing device performs the image filter processing using a three-dimensional image filter.

8. The X-ray CT apparatus according to claim 1, wherein the image filter processing device performs the image filter processing using one of a two-dimensional image filter and a one-dimensional filter.

9. The X-ray CT apparatus according to claim 1, wherein the image filter processing device dynamically varies the image filter processing with a change in the cross sectional direction of the two-dimensional image to be displayed while the three-dimensional tomographic image is displayed.

10. The X-ray CT apparatus according to claim 1, wherein the image filter processing device comprises an optimizing device configured to optimize a processing direction of the image filter processing on the three-dimensional tomographic image while the three-dimensional tomographic image is displayed.

11. A method for image filter processing a three-dimensional image, wherein a two-dimensional image is extracted from a three-dimensional image, said method comprising:
    defining a pixel of interest and a plurality of pixels neighboring the pixel of interest using an image filter processing device, the plurality of neighboring pixels positioned with respect to the pixel of interest in a direction orthogonal to the two-dimensional image;
    determining pixel values for the plurality of neighboring pixels surrounding the pixel of interest;
    determining an overall standard deviation for the plurality of neighboring pixels;
    determining a minimum standard deviation using the overall standard deviation;
    comparing the overall standard deviation to the minimum standard deviation to determine a shape characteristic value;
    multiplying the minimum standard deviation and an adjustable coefficient to generate a minimum threshold value and a maximum threshold value; and
    filter processing the three-dimensional image using the image filter processing device, wherein said filter processing is performed for the pixel of interest and varies depending on the shape characteristic, quantity of the plurality of neighboring pixels.

12. A method in accordance with claim 11, further comprising sorting the plurality of neighboring pixels in ascending numeric order.

13. A method in accordance with claim 11 further comprising determining at least one weight coefficient using the minimum threshold value and the maximum threshold value and normalizing the weight coefficients.

14. A method in accordance with claim 11 further comprising smoothing the plurality of neighboring pixels to facilitate sharpening a boundary between structures and to perform edge enhancement.

* * * * *

UNITED STATES PATENT AND TRADEMARK OFFICE
CERTIFICATE OF CORRECTION

PATENT NO.       : 8,009,890 B2
APPLICATION NO.  : 11/619242
DATED            : August 30, 2011
INVENTOR(S)      : Nishide et al.

It is certified that error appears in the above-identified patent and that said Letters Patent is hereby corrected as shown below:

In Column 13, Line 12, in Equation (10), delete "v(–l),v(–/+l+1)," and insert -- v($-l$),v($-l+1$), --, therefor.

In Column 15, Line 11, delete "max are" and insert -- max [....] are --, therefor.

In Column 28, Line 50, in Claim 11, delete "characteristic," and insert -- characteristic --, therefor.

Signed and Sealed this
Fourteenth Day of February, 2012

David J. Kappos
*Director of the United States Patent and Trademark Office*